US012582711B2

(12) United States Patent
Iversen et al.

(10) Patent No.: US 12,582,711 B2
(45) Date of Patent: Mar. 24, 2026

(54) RNA-BASED ADJUVANT TO ENHANCE THE IMMUNE RESPONSE TO VACCINES AND THERAPEUTICS

(71) Applicant: ImmuneSure LLC, Lebanon, OR (US)

(72) Inventors: Patrick Iversen, Grand Junction, CO (US); Nickolas Kipshidze, New York, NY (US); Nodar Kipshidze, New York, NY (US)

(73) Assignee: IMMUNESURE LLC, Lebanon, OR (US)

( * ) Notice: Subject to any disclaimer, the term of this patent is extended or adjusted under 35 U.S.C. 154(b) by 119 days.

(21) Appl. No.: 17/820,623

(22) Filed: Aug. 18, 2022

(65) Prior Publication Data

US 2023/0165954 A1     Jun. 1, 2023

Related U.S. Application Data

(60) Provisional application No. 63/241,257, filed on Sep. 7, 2021, provisional application No. 63/235,527, filed on Aug. 20, 2021, provisional application No. 63/234,857, filed on Aug. 19, 2021.

(51) Int. Cl.
| | |
|---|---|
| *A61K 39/39* | (2006.01) |
| *A61P 37/04* | (2006.01) |
| *C12N 15/113* | (2010.01) |
| *A61K 39/00* | (2006.01) |

(52) U.S. Cl.
CPC .............. *A61K 39/39* (2013.01); *A61P 37/04* (2018.01); *C12N 15/1136* (2013.01); *A61K 2039/55561* (2013.01); *C12N 2310/11* (2013.01); *C12N 2310/3125* (2013.01); *C12N 2310/321* (2013.01); *C12N 2310/3233* (2013.01)

(58) Field of Classification Search
CPC .......... A61K 39/39; A61K 2039/55561; A61K 2039/55527; A61K 39/04; A61K 2039/53; A61K 39/0208; A61P 37/04; A61P 31/06; C12N 15/1136; C12N 2310/11; C12N 2310/3125; C12N 2310/321; C12N 2310/3233; C12N 15/1138; C12N 2310/3513; C12N 2320/31; Y02A 50/30
See application file for complete search history.

(56) References Cited

U.S. PATENT DOCUMENTS 7,989,608 B2 *   8/2011   Mourich ................. A61P 31/12
536/23.1

OTHER PUBLICATIONS

Crooke ST. Antisense Drug Technology: Principles, Strategies, and Applications, Second Edition. 2nd ed. Milton: CRC Press, 2008. Web. (Year: 2008).*
Wang M, Wu B, Shah SN, Lu P, Lu Q. Aminoglycoside Enhances the Delivery of Antisense Morpholino Oligonucleotides In Vitro and in mdx Mice. Mol Ther Nucleic Acids. 2019; 16:663-674. (Year: 2019).*

(Continued)

*Primary Examiner* — Joanne Hama
*Assistant Examiner* — Hannah Sunshine
(74) *Attorney, Agent, or Firm* — Michael Best & Friedrich LLP

(57) ABSTRACT

Described herein are antisense inhibitor adjuvant compositions comprising modified nucleotide sequences complementary to a *Homo sapiens* interleukin 10 (IL-10) or interleukin 10 receptor alpha (IL-10RA) genes and methods for use thereof.

22 Claims, 6 Drawing Sheets

Specification includes a Sequence Listing.

(56) References Cited

OTHER PUBLICATIONS

Yoshida T, Naito Y, Yasuhara H, et al. Evaluation of off-target effects of gapmer antisense oligonucleotides using human cells. Genes Cells. 2019;24(12):827-835. (Year: 2019).*

Abers, et al., "An immune-based biomarker signature is associated with mortality in COVID-19 patients," JCI Insight, vol. 6, No. 1, 2021, (21 pages).

Adikari, et al., "Dengue NS1 antigen contributes to disease severity by inducing interleukin (IL)-10 by monocytes," Clinical & Experimental Immunology, vol. 184, Issue 1, Apr. 2016, (pp. 90-100).

Autran, et al., "Therapeutic Vaccines for Chronic Infections," Science, vol. 305, No. 5681, Jul. 9, 2004, (pp. 205-208).

Baize, et al., "Inflammatory responses in Ebola virus-infected patients," Clinical & Experimental Immunology, vol. 128, Issue 1, Apr. 2002, (pp. 163-168).

Barthelemy, et al., "Influenza A virus-induced release of interleukin-10 inhibits the anti-microbial activities of invariant natural killer T cells during invasive pneumococcal superinfection," Mucosal Immunology, vol. 10, No. 2, Mar. 2017, (pp. 460-469).

Brady, et al., "Hepatitis C virus non-structural protein 4 suppresses Th1 responses by stimulating IL-10 production from monocytes," European Journal of Immunology, vol. 33, No. 12, Nov. 19, 2003, (pp. 3448-3457).

Brooks, et al., "IL-10 blockade facilitates DNA vaccine-induced T cell responses and enhances clearance of persistent virus infection," The Journal of Experimental Medicine, vol. 205, No. 3, Mar. 17, 2008, (pp. 533-541).

Brooks, et al., "Interleukin-10 determines viral clearance or persistence in vivo," Nat Med., vol. 12, No. 11, Nov. 2006, (pp. 1301-1309).

Clerici, et a., "Role of interleukin-10 in T helper cell dysfunction in asymptomatic individuals infected with the human immunodefiniency virus," The Journal of Clinical Investigation, vol. 93, No. 2, 1994, (pp. 768-775).

Dhar, et al., "IL-6 and IL-10 as predictors of disease severity in COVID-19 patients: results from meta-analysis and regression," Heliyon, vol. 7, No. 2, Feb. 2021, (9 pages).

Diao, et al., "Reduction and Functional Exhaustion of T Cells in Patients With Coronavirus Disease 2019 (COVID-19)," Frontiers in Immunology, vol. 11, Article 827, published May 1, 2020, (7 pages).

Fan, et al., "Characterization of SARS-CoV-specific memory T cells from recovered individuals 4 years after infection," Archives of Virology, vol. 154, No. 7, published Jun. 13, 2009, (pp. 1093-1099).

Faure, et al., "Distinct immune response in two MERS-CoV-infected patients: can we go from bench to bedside?" PLoS One, vol. 9, No. 2, published Feb. 14, 2014, (7 pages).

Klenerman, et al., "T cells and viral persistence: lessons from diverse infections," Nature Immunology, vol. 6, No. 9, Sep. 2005, (pp. 873-879).

Kwilasz, et al., "The therapeutic potential of interleukin-10 in neuroimmune diseases," Neuropharmacology, vol. 96, Pt A, Sep. 2015, (pp. 55-69).

Landay, et al., "In vitro restoration of T cell immune functions in human immunodeficiency virus-positive persons: effects of interleukin (IL)-12 and anti-IL-10," The Journal of Infectious Diseases, vol. 173, Issue 5, May 1996, (pp. 1085-1091).

Li, et al., "SARS-CoV-2 and viral sepsis: observations ans hypotheses," Lancet, vol. 395, No. 10235, published Apr. 17, 2020 (pp. 1517-1520).

Li, et al., "The relationship between serum interleukins and T-lymphocyte subsets in patients with severe acute respiratory syndrome," Chinese Medical Journal, vol. 116, No. 7, Jul. 2003, (pp. 981-984).

Lu, et al., "A Potential Role of Interleukin 10 in COVID-19 Pathogenesis," Trends in Immunology, vol. 42, No. 1, Jan. 2021, (pp. 3-5).

Luo, et al., "Interleukin-10 inhibits Mycobacterium bovis bacillus Calmette-Guerin (BCG)-induced macrophage cytotoxicity against bladder cancer cells," Clinical & Experimental Immunology, vol. 160, No. 3, 2010, (pp. 359-368).

Mohanty, et al., "Prolonged Proinflammatory Cytokine Production in Monocytes Modulated by Interleukin 10 After Influenza Vaccination in Older Adults," The Journal of Infectious Diseases, vol. 211, No. 7, 2015, (pp. 1174-1184).

Panchal, et al., "Induced IL-10 Splice Altering Approach to Antiviral Drug Discovery," Nucleic Acid Therapeutics, vol. 24, No. 3, published 2014, (pp. 179-185).

Reynard, et al., "Immune parameters and outcomes during Ebola virus disease," JCI Insight, vol. 4, No. 1, Jan. 10, 2019, (15 pages).

Rico, et al., "Hepatitis B Virus-Specific T-Cell proliferation and Cytokine Secretion in Chronic Hepatitis B e Antibody-Positive Patients Treated With Ribavirin and Interferon Alpha," Hepatology, vol. 33, No. 1, 2001, (pp. 295-300).

Stober, et al., "IL-10 from regulatory T cells determines vaccine efficacy in murine Leishmania major infection," The Journal of Immunology, vol. 175, No. 4, published Aug. 15, 2005, (pp. 2517-2524).

Sun, et al., "A Detrimental Effect of Interleukin-10 on Protective Pulmonary Humoral Immunity during Primary Influenza A Virus Infection," Journal of Virology, vol. 84, No. 10, May 2010, (pp. 5007-5014).

Van Der Sluijs, et al., "IL-10 is an important mediator of the enhanced susceptibility to pneumococcal pneumonia after influenza infection," The Journal of Immunology, vol. 172, No. 12, Jun. 15, 2004, (pp. 7603-7609).

Villinger, et al., "Markedly elevated levels of interferon (IFN)-gamma, IFN-alpha, interleukin (IL)-2, IL-10, and tumor necrosis factor-alpha associated with fatal Ebola virus infection," The Journal of Infectious Diseases, vol. 179, Issue Supplement 1, Feb. 1999, (pp. S188-S191).

Xu, et al., "IL-10 Dampens the Th1 and Tc Activation through Modulating DC Functions in BCG Vaccination," Mediators of Inflammation, vol. 2019, ID 8616154, published Jun. 12, 2019, (10 pages).

Xu, et al., "Pathological findings of COVID-19 associated with acute respiratory distress syndrome," The Lancet Respiratory Medicine, vol. 8, No. 4, Apr. 2020, (pp. 420-422).

Zhu, "SARS Immunity and Vaccination," Cellular & Molecular Immunology, vol. 1, No. 3, Jun. 2004, (pp. 193-198).

* cited by examiner

FIG. 2

IL-10 AUG 54-75
SEQ ID NO: 13 mRNA    5'-gaaggcatgcacagccagcac-3'

SEQ ID NO: 14

Oligomer    3'-CTTCCGTACGTGTCG GTCGTC-5 mRNA 3' End

Oligomer 5' End

Blebmar

Large Ribosome Subunit

Small Ribosome Subunit tRNA

Oligomer 3' End mRNA 5' End

FIG. 3A

*Homo sapiens* interleukin 10 (IL10), RefSeqGene (LRG_1230) on chromosome 1.
NCBI Reference Sequence: NG_012088.1 (SEQ ID NO: 15)

```
mRNA  join  (1..224,  1080..1139,  1436..1588,  2601..2666,  3767..4893)
/gene="IL10"

CDS  join  (60..224,  1080..1139,  1436..1588,  2601..2666,  3767..3859)
/gene="IL10"

1 acacatcagg ggcttgctct tgcaaaacca aaccacaaga cagacttgca aaagaaggca
  61 tgcacagctc agcactgctc tgttgcctgg tcctcctgac tggggtgagg gccagcccag
 121 gccagggcac ccagtctgag aacagctgca cccacttccc aggcaacctg cctaacatgc
 181 ttcgagatct ccgagatgcc ttcagcagag tgaagacttt ctttgtgagt atgattcctt
1021 accgcatttc agttatttcc ccaaacctca agttcattct ccttttgttc ttcctgcag/c
1081 aaatgaagga ttagctggac aacttgttgt taaaggagtc cttgctggag gactttaagg
1141 tgagagcagg ggcggggtgc tggggggagtg tgcagcatga ttaaggagg ggagactctg
1201 cttcctgatt gcagggaatt gggtttgttt ccttcgcttt gaaaaggaga agtgggaaga
1261 tgttaactca gcacatccag cagccagagg gtttacaaag ggctcagtcc cttcggggag
1321 gcttctggtg aaggaggatc gctagaacca agctgtcctc ttaagctagt tgcagcagcc
1381 cctcctccca gccacctccg ccaatctctc actcacttt ggctcctgcc cttag/gtta
1441 cctgggttgc caagccttgt ctgagatgat ccagttttac ctggaggagg tgatgcccca
1501 agctgagaac caagacccag acatcaaggc gcatgtgaac tccctggggg agaacctgaa
1561 gaccctcagg ctgaggctac ggcgctgtgt aagtagcaga tcagttttt cccttgcagc
2581 ctttctcttt tcttccacag catcgatttc ttccctgtga aaacaagagc aaggccgtgg
2641 agcaggtgaa gaatgccttt aataaggtga gcttggatgg tggcagagag ggtctgcaga
3721 tccccagaaa ggattttaac tgtatgtttc ttatctctct gcacag/ctcc aagagaaagg
3781 catctacaaa gccatgagtg agtttgacat cttcatcaac tacatagaag cctacatgac
3841 aatgaagata cgaaactgag acatcagggt ggcgactcta tagactctag gacataaatt
```

FIG. 3B

Oligomer Sequences 5′→3′

| | | | |
|---|---|---|---|
| IL-10 E4SA 2592–2613 | GGAGAAATCGATGCTGTGGAA | 21 | (SEQ ID NO: 1) |
| IL-10 AUG 54–75 | GTGCTGGCTGTGCATGCCTTC | 22 | (SEQ ID NO: 2) |
| IL-10 E2SA 1071–1092 | GATCCTTCTTTGCTGCAGGAA | 21 | (SEQ ID NO: 3) |
| IL-10 E3SA 1426–1446 | CCCGGTAACCCTAAGGGCAG | 20 | (SEQ ID NO: 4) |
| IL-10 E4SA 2591–2613 | GGAGAAATCGATGCTGTGGAAG | 22 | (SEQ ID NO: 5) |
| IL-10 E5SA 3757–3780 | CCTTTCCTTGGAGCTGTGCAGAG | 23 | (SEQ ID NO: 6) |
| IL-10 E4SA 2591–2613 ᴹᵉC | GGAGAAATᴹᵉCGATGCTGTGGAAG | 23 | (SEQ ID NO: 11) |

IL-10 AUG 54–75 (SEQ ID NO: 2)

```
                t
gaaggcatgcacagc cagcac
::::::::::::::: ::::::
CTTCCGTACGTGTCG GTCGTG
```

IL-10 E2SA 1071–1092 (SEQ ID NO: 3)

```
           t
ttcctgcag/caaa gaaggatc
::::::::: :::: ::::::::
AAGGACGTC GTTT CTTCCTAG
```

IL-10 E3SA 1426–1446 (SEQ ID NO: 4)

```
               t
ctgcccttag/ggttacc ggg
:::::::::: ::::::: :::
GACGGGAATC CCAATGG CCC
```

IL-10 E4SA 2591–2613 (SEQ ID NO: 5) (analogus to SEQ ID NO: 1 - 2592–2613)

```
               t
cttccaca/catcgatttct cc
:::::::: :::::::::::: ::
GAAGGTGTCGTAGCTAAAGA GG
```

IL-10 E5SA 3757–3780 (SEQ ID NO: 6)

```
                 a
ctctgcacag/ctccaag gaaagg
:::::::::: ::::::: ::::::
GAGACGTGTC GAGGTTC CTTTCC
```

IL-10 E4SA 2591–2613 (SEQ ID NO: 11)

```
cttccaca/catcgatttcttcc
:::::::: :::::::::::::::
GAAGGTGTCGTAGCTAAAGAAGG     (bold italic C = ᴹᵉC)
```

FIG. 4A

*Homo sapiens* interleukin 10 receptor subunit alpha (IL10RA)
NCBI Reference Sequence: NG_016275.1 (SEQ ID NO: 16)

mRNA   join(1..144,   1992..2112,   3052..3230,   6851..7020,   7609..7759,
9199..9320, 12325..15093) /gene="IL10RA"

CDS   join (78..144,   1992..2112,   3052..3230,   6851..7020,   7609..7759,
9199..9320, 12325..13251) /gene="IL10RA"

```
  61    gatgcggcgc gcccaggatg ctgccgtgcc tcgtagtgct gctggcggcg ctcctcagcc
 121    tccgtcttgg ctcagacgct catggtaagg ctccgggacg cggcccttcc ctgccctgcc
1981    cttctcccca g/ggacagagc tgcccagccc tccgtctgtg tggtttgaag cagaattttt
2041    ccaccacatc ctccactgga cacccatccc aaatcagtct gaaagtacct gctatgaagt
2101    ggcgctcctg aggtgaggaa aagggaagag ggaggggggag ggaggagtga atccccgcct
3001    gtaggattga gcacaagctc gtttccagtg cctaacctgg tatctcctca g/gtatggaat
3061    agagtcctgg aactccatct ccaactgtag ccagaccctg tcctatgacc ttaccgcagt
3121    gaccttggac ctgtaccaca gcaatggcta ccgggccaga gtgcgggctg tggacggcag
3181    ccggcactcc aactggaccg tcaccaacac ccgcttctct gtggatgaag gtgcttttcc
3241    tcccttgact tagaacatgg ctctgaagtc ccttccagcc aggaactcta gtctagagct
3301    tttctgtcta ttaccatagc tcaccatgtc tgccagcctc cctggccgga gaactagttg
6541    ccatttgttg aagagactgt tctttttccca ttgtgtgttc ttggcccctt tgttgaaaat
6601    caattgtggg tttatttctg ggctgtccat catattccat tggttgatgc atctgatttt
6661    agggtatatg tatttttaat gtgctcccca agaagtcctt acattctgct gcattgacaa
6721    acctgtggcc aagttttagg cctaggttct aattaagctt aattctggag gcaaagtctc
6781    ggcggggaca cccaggccct cctcagccct caagtctcat ggtattcccc cccaccccaa
6841    ctccatttag tgactctgac agttggcagt gtgaacctag agatccacaa tggcttcatc
6901    ctcgggaaga ttcagctacc caggcccaag atggcccccg caaatgacac atatgaaagc
6961    atcttcagtc acttccgaga gtatgagatt gccattcgca aggtgccggg aaacttcacg
7021    gtatggggtt ccccaaggcc ccagggccag aactcccttg gcttccctgt ccctgggct
```

FIG. 4B

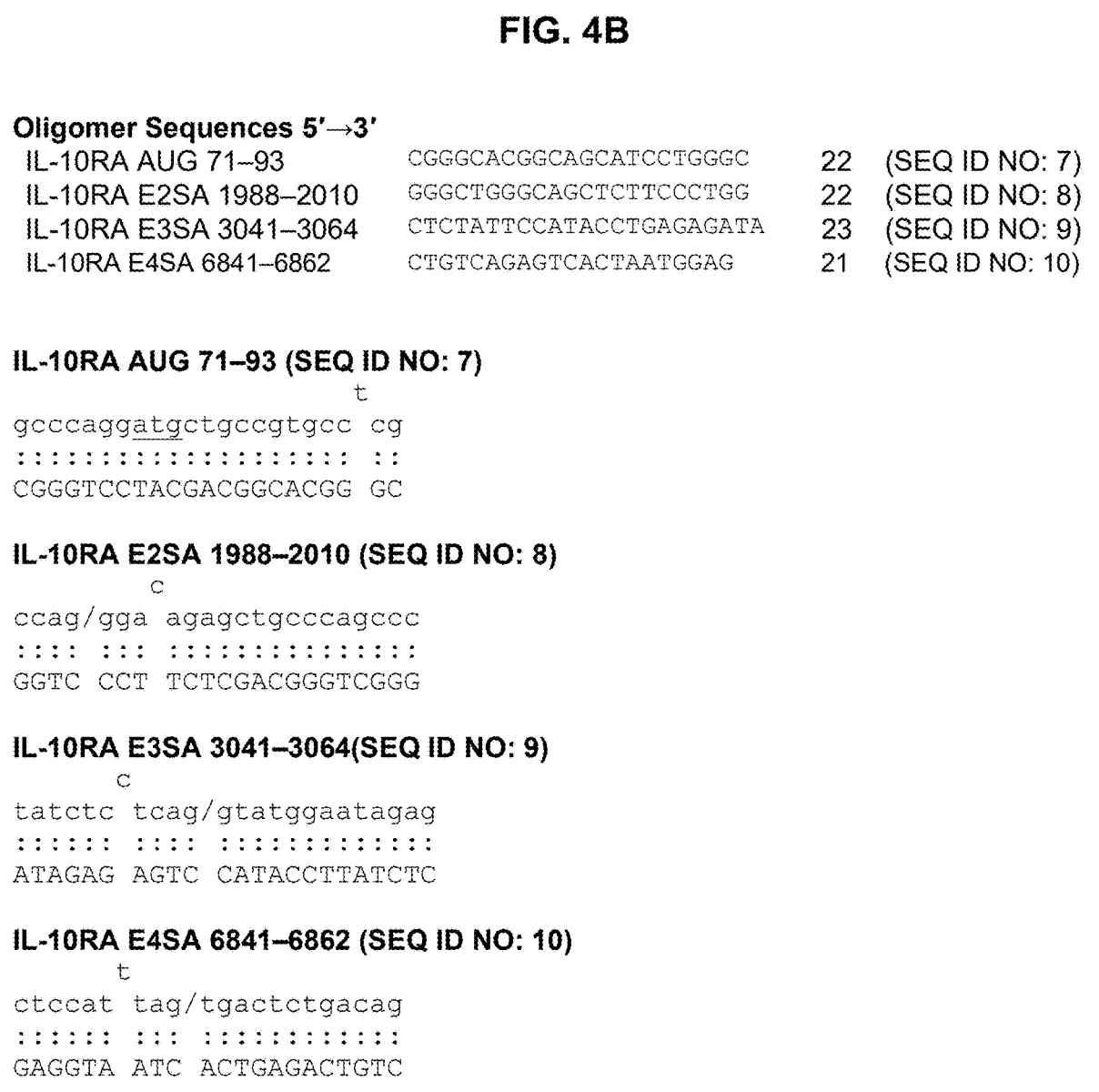

Oligomer Sequences 5'→3'

| | | | |
|---|---|---|---|
| IL-10RA AUG 71–93 | CGGGCACGGCAGCATCCTGGGC | 22 | (SEQ ID NO: 7) |
| IL-10RA E2SA 1988–2010 | GGGCTGGGCAGCTCTTCCCTGG | 22 | (SEQ ID NO: 8) |
| IL-10RA E3SA 3041–3064 | CTCTATTCCATACCTGAGAGATA | 23 | (SEQ ID NO: 9) |
| IL-10RA E4SA 6841–6862 | CTGTCAGAGTCACTAATGGAG | 21 | (SEQ ID NO: 10) |

IL-10RA AUG 71–93 (SEQ ID NO: 7)

```
                    t
gcccaggatgctgccgtgcc cg
:::::::::::::::::::: ::
CGGGTCCTACGACGGCACGG GC
```

IL-10RA E2SA 1988–2010 (SEQ ID NO: 8)

```
         c
ccag/gga agagctgcccagccc
:::: ::: :::::::::::::::
GGTC CCT TCTCGACGGGTCGGG
```

IL-10RA E3SA 3041–3064(SEQ ID NO: 9)

```
       c
tatctc tcag/gtatggaatagag
:::::: :::: :::::::::::::
ATAGAG AGTC CATACCTTATCTC
```

IL-10RA E4SA 6841–6862 (SEQ ID NO: 10)

```
      t
ctccat tag/tgactctgacag
:::::: ::: ::::::::::::
GAGGTA ATC ACTGAGACTGTC
```

RNA-BASED ADJUVANT TO ENHANCE THE IMMUNE RESPONSE TO VACCINES AND THERAPEUTICS

CROSS-REFERENCE TO RELATED APPLICATIONS

This application claims priority to U.S. Provisional Patent Application Nos. 63/234,857, filed on Aug. 19, 2021; U.S. 63/235,527, filed on Aug. 20, 2021; and U.S. 63/241,257, filed on Sep. 7, 2021, each of which is incorporated by reference herein in its entirety.

REFERENCE TO SEQUENCE LISTING

This application was filed with a Sequence Listing XML in ST.26 XML format accordance with 37 C.F.R. § 1.831. The Sequence Listing XML file submitted in the USPTO Patent Center, "890029-0002-US04_sequence_listing_xml_4 Nov. 2025.xml" was created on Nov. 4, 2025, contains 17 sequences, has a file size of 19.8 kilobytes (20,304 bytes), and is incorporated by reference in its entirety into the specification.

TECHNICAL FIELD

Described herein are antisense inhibitor adjuvant compositions comprising modified nucleotide sequences complementary to a *Homo sapiens* interleukin 10 (IL-10) or interleukin 10 receptor alpha (IL-10RA) genes and methods for use thereof.

BACKGROUND

IL-10 is an anti-inflammatory glycoprotein that participates in the regulation of immunity. IL-10 inhibits the activity of Th1 cells (a sub population of CD4$^+$ T-cells), natural killer T-cells (NK), and macrophages that contribute to clearance of infected cells. Expression and secretion of IL-10 inhibits the synthesis of interferon gamma (IFN-gamma), IL-2, IL-3, tumor necrosis factor (TNF), and GM-CSF produced by activated macrophages and helper T-cells resulting in the inhibition of immune responses participating in clearance of virally infected cells. Several immune cell type express IL-10 including macrophages, dendritic cells, B-cells, and subsets of CD4$^+$ and CD8$^+$ T-cells.

An antisense oligonucleotide designed to bind to the splice acceptor region of exon four of IL-10 pre-mRNA (5'-GGAGAAATCGATGCTGTGGA-3'; IL-10E4SA, SEQ ID NO: 1) led to skipping of exon 4 in the mature mRNA and reduced translation to the IL-10 protein. The IL10E4SA was determined to be optimal in targeting a variety of IL-10 transcript sites [1]. The inhibition of IL-10 protein in freshly isolated bone-marrow derived cells cultured to promote differentiation into dendritic cells was sequence specific, dose, and time dependent. When administered to mice that were challenged with a lethal mouse adapted Ebola virus, a survival benefit was observed in 7 replicate experiments of 10 mice in each treatment group for a cumulative of 41 survivors in the 70 infected mice compared to less than 10 survivors in 70 infected mice in vehicle control groups. Antibody depletion studies in IL-10$^{-/-}$ mice suggest a role for NK cells and IFN-gamma for the improved immune response in clearing infected cells. The capacity to shift Th1/Th2 balance with IL-10E4SA antisense oligomers represents a unique adjuvant strategy.

What are needed are antisense inhibitor adjuvant compositions comprising nucleotide sequences complementary to a *Homo sapiens* interleukin 10 (IL-10) or interleukin 10 receptor alpha (IL-10RA) genes.

SUMMARY

One embodiment described herein is an antisense inhibitor adjuvant composition comprising a nucleotide sequence complementary to a *Homo sapiens* interleukin 10 (IL-10) or interleukin 10 receptor alpha (IL-10RA) gene, wherein the nucleotide sequence comprises one or more of: uniform modifications of each nucleotide with 2'-O-methyl, 2'-O-ethyl, or 2'-methoxyethyl substituents or uniform replacement of the ribose sugar with a morpholino subunit and phosphorous-containing intersubunit linkages, (PMO), dimethylamine-linked phosphate, or methylphosphonate; a free energy ($\Delta G$) of hybridization of $-25$ to $-35$ kcal/mol; and a single mismatch ("blebmer") with a target RNA to enhance the steric blocking of RNA function. In one aspect, the nucleotide sequence comprises a nucleic acid sequence with 90-99% identity to SEQ ID NO: 1-11. In another aspect, the nucleotide sequence comprises SEQ ID NO: 1-11. In another aspect, the antisense inhibitor is administered with one or more aminoglycosides. In another aspect, the aminoglycoside comprises one or more of Kanamycin A, Amikacin, Tobramycin, Dibekacin, Gentamicin, Sisomicin, Netilmicin, Neomycin B, Neomycin C, Neomycin E (paromomycin), Streptomycin, Plazomicin, or Neo-Fradin.

Another embodiment described herein is a method for suppressing an IL-10 immune response associated with a vaccine, the method comprising administering an antisense inhibitor adjuvant comprising an antisense inhibitor adjuvant composition as described herein. In one aspect, the vaccine is for an infectious disease selected from one or more of Herpes simplex, type 1; Herpes simplex, type 2; encephalitis virus, papillomavirus, Varicella-zoster virus; Epstein-Barr virus; Human cytomegalovirus; Human herpesvirus, type 8; Human papillomavirus; BK virus; JC virus; Smallpox; polio virus, Hepatitis B virus; Human bocavirus; Parvovirus B19; Human astrovirus; Norwalk virus; coxsackievirus; hepatitis A virus; poliovirus; rhinovirus; Hepatitis C virus; yellow fever virus; dengue virus; West Nile virus; Rubella virus; Hepatitis E virus; Human immunodeficiency virus (HIV); Influenza virus, type A or B; Guanarito virus; Junin virus; Lassa virus; Machupo virus; Sabiávirus; Crimean-Congo hemorrhagic fever virus; Ebola virus; Marburg virus; Measles virus; Mumps virus; Parainfluenza virus; Respiratory syncytial virus; Human metapneumovirus; Hendra virus; Nipah virus; Rabies virus; Hepatitis D; Rotavirus; Orbivirus; Coltivirus; Hantavirus; Coronavirus, including SARS-COV-2, Severe acute respiratory syndrome virus, and Middle East Respiratory Coronavirus; Chikungunya virus, Banna virus, Tuberculosis, or Leishmaniasis. In another aspect, the vaccine is for SARS-COV-2, Severe acute respiratory syndrome virus, Middle East Respiratory Coronavirus, Influenza, Ebola, Tuberculosis, or Leishmaniasis. In another aspect, adjuvant is administered prior to, concurrently with, or following administration of a vaccine. In another aspect, the adjuvant is administered orally, by injection, or by inhalation/insufflation. In another aspect, the adjuvant is administered with one or more second adjuvants. In another aspect, the second adjuvant comprises one or more of: cationic liposome-DNA complex JVRS-100, aluminum hydroxide vaccine adjuvant, aluminum phosphate vaccine adjuvant, aluminum potassium sulfate adjuvant, ALHDROGEL™, ISCOM(s)™, Freund's Complete Adjuvant, Freund's Incomplete Adjuvant, CpG DNA Vaccine Adjuvant, Cholera toxin, Cholera toxin B subunit, Liposomes, Saponin Vaccine Adjuvant, DDA Adjuvant, Squalene-based Adjuvants, Etx B subunit Adjuvant, IL-12 Vaccine Adjuvant, LTK63 Vaccine Mutant Adjuvant, TITERMAX™ Gold Adjuvant, Ribi Vaccine Adjuvant, Montanide ISA 720 Adjuvant, *Corynebacterium*-derived P40 Vaccine Adjuvant, MPL™ Adjuvant, AS04, AS02, Lipopolysaccharide Vaccine Adjuvant, Muramyl Dipeptide Adjuvant, CRL1005, Killed *Corynebacterium parvum* Vaccine Adjuvant, Montanide ISA 51, *Bordetella pertussis* component Vaccine Adjuvant, Cationic Liposomal Vaccine Adjuvant, Adamantylamide Dipeptide Vaccine Adjuvant, Arlacel A, VSA-3 Adjuvant, Aluminum vaccine adjuvant, Polygen Vaccine Adjuvant, ADJUMER™, Algal Glucan, Bay R1005, THERAMIDER, Stearyl Tyrosine, Specol, Algammulin, AVIRDINE®, Calcium Phosphate Gel, CTA1-DD gene fusion protein, DOC/Alum Complex, Gamma Inulin, Gerbu Adjuvant, GM-CSF, GMDP, Recombinant hIFN-gammaInterferon-g, Interleukin-1β, Interleukin-2, Interleukin-7, Sclavo peptide, REHYRDRAGEL™ LV, REHYRDRAGEL™ HPA, Loxoribine, MF59, MTP-PE Liposomes, Murametide, Murapalmitine, D-Murapalmitine, NAGO, Non-Ionic Surfactant Vesicles, PMMA, Protein Cochleates, QS-21, SPT (Antigen Formulation), nanoemulsion vaccine adjuvant, AS03, QUIL-A™ vaccine adjuvant, RC529 vaccine adjuvant, LTR192G Vaccine Adjuvant, *E. coli* heat-labile toxin, LT, amorphous aluminum hydroxyphosphate sulfate adjuvant, Calcium phosphate vaccine adjuvant, Montanide Incomplete Seppic Adjuvant, Imiquimod, Resiquimod, AF03, Flagellin, Poly(I:C), ISCOMATRIX®, Abisco-100 vaccine adjuvant, Albumin-heparin microparticles vaccine adjuvant, AS-2 vaccine adjuvant, B7-2 vaccine adjuvant, DHEA vaccine adjuvant, Immunoliposomes Containing Antibodies to Costimulatory Molecules, SAF-1, Sendai Proteoliposomes, Sendai-containing Lipid Matrices, Threonyl muramyl dipeptide (TMDP), Ty Particles vaccine adjuvant, Bupivacaine vaccine adjuvant, DL-PGL (Polyester poly (D,L-lactide-co-glycolide)) vaccine adjuvant, IL-15 vaccine adjuvant, TK72 vaccine adjuvant, MPL-SE vaccine adjuvant, non-toxic mutant E112K of Cholera Toxin mCT-E112K, and/or Matrix-S. In another aspect, the antisense inhibitor is administered with one or more aminoglycosides. In another aspect, the aminoglycoside comprises one or more of Kanamycin A, Amikacin, Tobramycin, Dibekacin, Gentamicin, Sisomicin, Netilmicin, Neomycin B, Neomycin C, Neomycin E (paromomycin), Streptomycin, Plazomicin, or Neo-Fradin.

Another embodiment described herein is a method for suppressing an IL-10 immune response as a treatment of a viral, bacterial, or other pathogen infection, comprising administering an antisense inhibitor composition as described herein. In one aspect, the viral, bacterial, or other pathogen infection is selected from one or more of Herpes simplex, type 1; Herpes simplex, type 2; encephalitis virus, papillomavirus, Varicella-zoster virus; Epstein-Barr virus; Human cytomegalovirus; Human herpesvirus, type 8; Human papillomavirus; BK virus; JC virus; Smallpox; polio virus, Hepatitis B virus; Human bocavirus; Parvovirus B19; Human astrovirus; Norwalk virus; coxsackievirus; hepatitis A virus; poliovirus; rhinovirus; Hepatitis C virus; yellow fever virus; dengue virus; West Nile virus; Rubella virus; Hepatitis E virus; Human immunodeficiency virus (HIV); Influenza virus, type A or B; Guanarito virus; Junin virus; Lassa virus; Machupo virus; Sabiávirus; Crimean-Congo hemorrhagic fever virus; Ebola virus; Marburg virus; Measles virus; Mumps virus; Parainfluenza virus; Respiratory syncytial virus; Human metapneumovirus; Hendra virus; Nipah virus; Rabies virus; Hepatitis D; Rotavirus; Orbivirus; Coltivirus; Hantavirus; Coronavirus, including SARS-COV-2, Severe acute respiratory syndrome virus, and Middle East Respiratory Coronavirus; Chikungunya virus, Banna virus, Tuberculosis, or Leishmaniasis. In another aspect, the viral, bacterial, or other pathogen infection is selected from SARS-COV-2, Severe acute respiratory syndrome virus, Middle East Respiratory Coronavirus, Influenza, Ebola, Tuberculosis, or Leishmaniasis. the antisense inhibitor is administered with one or more therapeutics. In another aspect, the antisense inhibitor is administered prior to, concurrently with, or following administration of a therapeutic. In another aspect, the antisense inhibitor is administered orally, by injection, or by inhalation/insufflation. In another aspect, the antisense inhibitor is administered with one or more aminoglycosides. In another aspect, the aminoglycoside comprises one or more of Kanamycin A, Amikacin, Tobramycin, Dibekacin, Gentamicin, Sisomicin, Netilmicin, Neomycin B, Neomycin C, Neomycin E (paromomycin), Streptomycin, Plazomicin, or Neo-Fradin.

BRIEF DESCRIPTION OF THE DRAWINGS

FIG. 2 illustrates the hybrid duplex of target RNA (SEQ ID NO: 14) and oligomer (SEQ ID NO: 15) interfering with the assembly of the ribosomal complex (or the spliceosomal complex) on the RNA thus disrupting their function.

FIG. 3A illustrates antisense targeting sites in the human IL-10 mRNA (NCBI Reference Sequence: NG_012088.1; SEQ ID NO: 15) (highlighted/underlined). FIG. 3B illustrates antisense oligonucleotide sequences and their pairing with IL-10 mRNA. Blebmer bases indicated on top line. The translation start site is underlined. The splice site is indicated by "/".

FIG. 4A illustrates antisense targeting sites in the human IL-10RA mRNA (NCBI Reference Sequence: NG_016275.1; SEQ ID NO: 16) (highlighted/underlined). FIG. 4B illustrates antisense oligonucleotide sequences and their pairing with IL-10RA mRNA. Blebmer bases indicated on top line. The translation start site is underlined. The splice site is indicated by "/".

DETAILED DESCRIPTION

Figure 1:
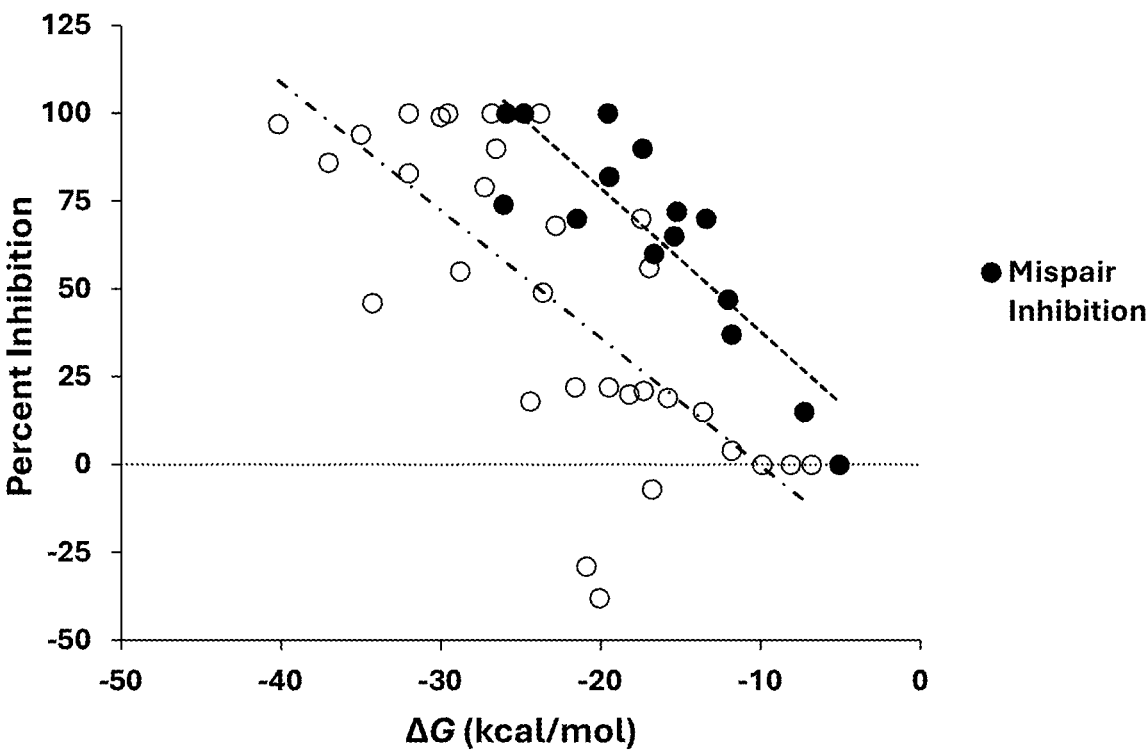
FIG. 1 illustrates steric blockers. Each circle represents a different oligomer. Filled circles incorporate mismatch sequences with target RNA. Open circles represent oligomers of varying length. ΔG is calculated by nearest neighbor analysis. A mismatch oligomer can achieve full penetrance at ΔG of −22 kcal/mole but a shortened oligomer will not achieve full penetrance until ΔG is −35 kcal/mole. This difference is evidence of special requirements of steric blockade.

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present disclosure, including definitions, will control. Exemplary methods and materials are described below, although methods and materials similar or equivalent to those described herein can be used in practice or testing of the embodiments and aspects described herein.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to +10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to +10% of any value within the range or within 3 or more standard deviations, including the end points.

As used herein, the terms "active ingredient" or "active pharmaceutical ingredient" refer to a pharmaceutical agent, active ingredient, compound, or substance, compositions, or mixtures thereof, that provide a pharmacological, often beneficial, effect.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the term "dose" denotes any form of an active ingredient formulation or composition, including cells, that contains an amount sufficient to initiate or produce a therapeutic effect with at least one or more administrations. "Formulation" and "composition" are used interchangeably herein.

As used herein, the term "prophylaxis" refers to preventing or reducing the progression of a disorder, either to a statistically significant degree or to a degree detectable by a person of ordinary skill in the art.

As used herein, the terms "effective amount" or "therapeutically effective amount," refers to a substantially non-toxic, but sufficient amount of an agent, composition, or cell(s) being administered to a subject that will prevent, treat, or ameliorate to some extent one or more of the symptoms of the disease or condition being experienced or that the subject is susceptible to contracting. The result can be the reduction or alleviation of the signs, symptoms, or causes of a disease, or any other desired alteration of a biological system. An effective amount may be based on factors individual to each subject, including, but not limited to, the subject's age, size, type or extent of disease, stage of the disease, route of administration, the type or extent of supplemental therapy used, ongoing disease process, and type of treatment desired.

As used herein, the term "subject" refers to an animal. Typically, the subject is a mammal. A subject also refers to primates (e.g., humans, male or female; infant, adolescent, or adult), non-human primates, rats, mice, rabbits, pigs, cows, sheep, goats, horses, dogs, cats, fish, birds, and the like. In one embodiment, the subject is a primate. In one embodiment, the subject is a human.

As used herein, a subject is "in need of treatment" if such subject would benefit biologically, medically, or in quality of life from such treatment. A subject in need of treatment does not necessarily present symptoms, particular in the case of preventative or prophylaxis treatments.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifest.

The terms below and used herein, have the following meanings, unless otherwise indicated:

"Antigen" is a molecule that will trigger an immune response, abbreviated by "Ag." An Ag may originate from within the body (a self-protein) or from an external site (non-self). The immune system may not react to self-proteins due to negative selection of T-cells in the thymus during development.

"Negative selection" is a process in which lymphocytes, capable of strong binding with self-protein defined by the major histocompatibility complex (MHC) are removed by receiving an apoptosis signal leading to cell death. Some lymphocytes are phagocytosed by dendritic cells which allows presentation of self-antigens to MHC class II, a requirement for CD4$^+$ T-cell negative selection. Some of these T-cells responding to self-proteins become Treg (T-regulatory) cells. The process is a component of central tolerance prevents formation of cells capable of inducing autoimmune diseases.

An "antibody" is a "Y" shaped protein, immunoglobulin (Ig), with an antigen binding site and an Fc region. Antibodies from humans include several classes or isotypes; IgA, IgD, IgE, IgG, or IgM. The IgG is composed of four polypeptide chains; two heavy chains and two light chains connected by disulfide bonds. The light chains contain one variable domain ($V_L$) and one constant domain (CL) and the heavy chains contain one variable domain (VH) and three to four constant domains (CH1, CH2, CH3). Structurally, an antibody has two antigen binding fragments (Fab) composed of VL, VH, CL, and CH1 and a Fc fragment forming the trunk of the Y.

A "T-Cell" is a type of white blood cells, a lymphocyte, that plays a central role in the Adaptive immune response. T-cells are differentiated from other lymphocytes by the presence of a T-cell receptor (TCR) on the cell surface. Multiple classes of T-cells are defined; CD8 killer T-cells, CD4 helper T-cells, and regulatory T-cells. Each class of T-cell performs a different function often involving release of cytokines. All T-cells originate from c-kit+Sca1$^+$ hematopoietic stem cells (HSC) that reside in the bone marrow.

An "epitope" is a structural feature of an antigen that is an antigenic determinant that matches an antibody recognition site.

"Vaccination" is the physical administration of a vaccine

"Immunization" is the provision of immunity by any means, active or passive

"Active immunization" is the administration of agents for induction of immunity that is long-lasting or at times, life-long.

"Passive immunization" is the administration of exogenously produced immune substances (e.g., convalescent serum, adoptive transfer of T-cells, or monoclonal antibodies) that dissipates with the turnover of the administered substances A "vaccine" is the conveyance of antigens to elicit immune responses that are generally protective. Multiple approaches to vaccine design are known including; attenuated virus, inactive virus, protein subunit, DNA vaccines, vectored vaccines, and mRNA vaccines.

"Vaccine adjuvant" is a substance that increases and/or modulates the immune response to a vaccine antigen. Adjuvants can be inorganic compounds (potassium alum, aluminum hydroxide, aluminum phosphate, calcium phosphate hydroxide), oils (paraffin oil, peanut oil, squalene), bacterial products (mycobacterium Boris, toxoids, lipopolysaccharides), plant products (saponins), cytokines (IL-1, IL-2, IL-12), and stimulators of innate immune responses by binding Toll receptors (TLR ligand including CpG motifs).

"RNA" is a ribonucleic acid and a polymeric molecule essential for coding, decoding, regulation and expression of genes. Cellular organisms use messenger RNA (mRNA) to convert genetic information as guanine (G), uracil (U), adenine (A), and cytosine (C) as triplets into selection of amino acids in synthesis of specific proteins "RNA vaccine" is a type of vaccine that uses a copy of a messenger RNA (mRNA) to express an antigen to produce an immune response as well as stimulate innate immune responses.

"Open reading frame" is the sequence of nucleic acid mRNA that is translated into protein. It is referred to as open to contrast reading frames containing termination codons.

"Untranslated region" is abbreviated as UTR and refers to sections of mRNA flanking the ORF. On the 5'-side it is the 5'-UTR or leader and on the 3'-side it is the 3'-UTR or trailer. The 5'-UTR contains sequence that is recognized by the ribosome and facilitates the initiation of translation. The 3'-UTR is located immediately after the translation termination codon and facilitates post-transcriptional modification.

Compounds capable of suppression of IL-10 or IL-10 signal transduction, including IL-10RA, JAK1, STAT3, and SOCS3, are associated with a more productive immune response to infection. Since multiple signaling pathways operate through JAK1, STA3, and SOCS3, these elements of the signal transduction pathway are less favored due to anticipated effects beyond those desired as a vaccine adjuvant. Suppression of IL-10 and/or IL-10RA are more focused in the desired vaccine adjuvant pathway. Further, the activation of transcription of IL-10 and IL-10RA upon immune stimulus means antisense inhibition can effectively prevent their translation and not rely on protein turnover for activity. The activity will be acute and transient, at or near the time of the activation of the immune response to infection or vaccination. IL-10 inhibits CB8$^+$ T cell responses by restricting T cell expansion during primary and memory responses to multiple types of infections. IL-10 can inhibit Th1 cells in the immune response by inhibiting IL-12 production and subsequent differentiation of Th1 cells. IL-10 and regulatory T cells act together to impair anti-tumor CD8$^+$ T cell effector differentiation.

Role in Persistent Viral Infections

As viral infections move from acute to persistence both CD4$^+$ and CD8$^+$ T cells become deleted or become nonfunctional. This is observed for HIV, HBV, and HCV infections as well as lymphocytic choriomeningitis virus (LCMV) infections in humans and rodents [2-5]. IL-10 production is increased during LCMV clone 13 (CI 13) infection in mice which serves as a model for persistent infection. T cell responses are retained after CI 13 infection in IL-10$^+$ mice including CD8$^+$ T cell function. Further, lack of viral persistence and rapid elimination of LCMV CI 13 was observed in the IL-10 deficient mice [6]. Antibody neutralization of IL-10 in PBMCs from cells HIV- and HCV-infected individuals also restored T-cell activities [7].

Role for Neutralizing IL-10 with a Vaccine

Vaccines to restore T cell activity for the control of persistent infections have not been successful [8]. Inhibition of IL-10R (IL-10 receptor) with a neutralizing antibody administered beginning on day 25 continued every 3 days for 2 weeks in conjunction with a DNA vaccine encoding LCMV-GP led to a 6-10-fold increase in virus specific CD4$^+$ and CD8$^+$ T-cells. The enhanced T-cell response was associated with a greater decrease in viral titers [9]. IL-10 is expressed at higher levels in elderly adults and is associated with impaired influenza vaccine responses [10].

Dengue is a rapidly emerging mosquito-borne flavivirus that can manifest as dengue hemorrhagic shock syndrome or dengue shock syndrome. Severe disease is associated with elevated IL-10 suppressed DENV-specific T cell responses [11].

Ebola and Marburg viruses are a highly lethal emerging filoviruses often manifesting in hemorrhagic fever. IL-10 is one of the highly expressed cytokines observed early after infection [12]. Studies in IL-10$^{-/-}$ mice and treated with antisense targeting IL-10 demonstrated improved survival benefit in mice infected with mouse adapted Ebola virus [1].

Contraindications for IL-10 Suppression

The neuroimmune diseases neuropathic pain, osteoarthritis, Parkinson's disease, and multiple sclerosis are associated with insufficient IL-10 [13].

Role in Acute Infections

Increased subject mortality from COVID-19 caused by the Coronavirus SARS COV-2 was significantly associated with multiple biomarkers which include IL-10 A novel feature of the COVID-19 cytokines storm is the elevation of IL-10 in severely ill subjects [15]. Progression of COVID-19 is associated with T cell exhaustion (PD-1$^+$/TIM3$^+$/CD8$^+$) and those cells are associated with serum IL-10 concentrations [16].

Antisense inhibitors of IL-10 and members of the IL-10 signal transduction pathway Embodiments described herein include co-administration of specified antisense inhibitors with a vaccine for the control of infectious disease. The antisense oligonucleotide targets IL-10, IL-10 receptor alpha, STAT3, SOCS3, and JAK1. The composition of the antisense oligonucleotide is designed to hybridize to the targeted pre-mRNA or mRNA to either block the RNA function through steric interference or bring about the degradation of the RNA through cellular recognition of the oligonucleotide: RNA duplex from RNAse H, RISC complex, or RNAse P enzymes.

Described herein are steric blocking antisense oligonucleotide compounds that are designed to interfere with RNA function. The compounds comprise: (i) modified RNA chemistry such as a ribose sugar modified at the 2'-position such as a 2'-O-methyl, 2'-O-ethyl, or 2'-methoxyethyl substituent or replacement of the ribose sugar with a morpholino subunit and phosphorous-containing intersubunit linkages; (ii) have a nucleotide sequence effective to hybridize to a target RNA with a free energy ($\Delta$G) of −25 to −35 kcal/mol; (iii) have a single mismatch with the target RNA to enhance the steric blocking of RNA function in what is referred to as a "blebmer"; (iv) the oligomer is formulated with a disruptor of ribosomal fidelity including compounds such as amino glycoside antibiotics. In one aspect, the blocking antisense oligonucleotide sequence are listed in Table 1 and comprise SEQ ID NO: 2-10. SEQ ID No 1 refers to a perfectly matching antisense phosphorodiamidate-linked morpholino oligomer (PMO) oligonucleotide with a cell penetrating peptide conjugated to the 3'-end. Each of the sequences (SEQ ID NO: 1-9) described herein encompasses a chemically modified sequence. The antisense oligonucleotide sequences can be DNA, RNA, hybrid, or chimeric oligonucleotides (having a mixture of deoxyribonucleotides and ribonucleotides) or have modified backbone chemistry such as peptide nucleic acid or phosphorodiamidate-linked morpholino oligomer (PMO) oligonucleotides.

TABLE 1

IL-10 and IL-10 Receptor Alpha Antisense Sequences

| Description | Sequence (5'→3')* | SEQ ID NO |
|---|---|---|
| IL-10 E4SA 2591-2613 | GGAGAAATCGATGCTGTGGAA | 1 |
| IL-10 AUG 54-75 | GTGCTGGCTGTGCATGCCTTC | 2 |
| IL-10 E2SA 1071-1092 | GATCCTTCTTTGCTGCAGGAA | 3 |

TABLE 1-continued

IL-10 and IL-10 Receptor Alpha Antisense Sequences

| Description | Sequence (5'→3')* | SEQ ID NO |
|---|---|---|
| IL-10 E3SA 1426-1446 | CCCGGTAACCCTAAGGGCAG | 4 |
| IL-10 E4SA 2591-2614 | GGAGAAATCGATGCTGTGGAAG | 5 |
| IL-10 E5SA 3757-3780 | CCTTTCCTTGGAGCTGTGCAGAG | 6 |
| IL-10RA AUG 71-93 | CGGGCACGGCAGCATCCTGGGC | 7 |
| IL-10RA E2SA 1988-2010 | GGGCTGGGCAGCTCTTCCCTGG | 8 |
| IL-10RA E3SA 3041-3064 | CTCTATTCCATACCTGAGAGATA | 9 |
| IL-10RA E4SA 6841-6862 | GGAGAAATCGATGCTGTGGAA | 10 |
| IL-10 E4SA 2591-2613 MeC | GGAAGAAAT$^{Me}$CGATGCTGTGGAAG | 11 |

*Sequences 1-11 are shown as DNA nucleotides herein and in the sequence listing, but may be RNA, hybrids or chimeric nucleotides, have modified backbones (PNA, PMO), or have modified sugar residues (e.g., 2'-O modifications).

A non-limiting list of infectious diseases that may be treated or prevented by a vaccine and be boosted with an IL-10 adjuvant includes, viral infectious diseases such as AIDS (HIV), HIV resulting in mycobacterial infection, AIDS related Cachexia, AIDS related Cytomegalovirus infection, HIV-associated nephropathy, Lipodystrophy, AID related cryptococcal meningitis, AIDS related neutropaenia, *Pneumocystis jiroveci* (*Pneumocystis carinii*) infections, AID related toxoplasmosis, hepatitis A, B, C, D or E, herpes, herpes zoster (chicken pox), German measles (rubella virus), yellow fever, dengue fever etc. (flavi viruses), flu (influenza viruses), haemorrhagic infectious diseases (Marburg or Ebola viruses), bacterial infectious diseases such as Legionnaires' disease (*Legionella*), gastric ulcer (*Helicobacter*), cholera (*Vibrio*), *E. coli* infections, Staphylococcal infections, *Salmonella* infections or Streptococcal infections, tetanus (*Clostridium tetani*), protozoan infectious diseases (malaria, sleeping sickness, leishmaniasis, toxoplasmosis, i.e., infections caused by plasmodium, trypanosomes, *leishmania* and toxoplasma), diphtheria, leprosy, measles, pertussis, rabies, tetanus, tuberculosis, typhoid, varicella, diarrheal infections such as Amoebiasis, *Clostridium difficile*-associated diarrhea (CDAD), Cryptosporidiosis, Giardiasis, Cyclosporiasis and Rotaviral gastroenteritis, encephalitis such as Japanese encephalitis, Wester equine encephalitis and Tick-borne encephalitis (TBE), fungal skin diseases such as candidiasis, onychomycosis, *Tinea captis*/scalp ringworm, *Tinea corporis*/body ringworm, *Tinea cruris*/jock itch, sporotrichosis and *Tinea pedis*/Athlete's foot, Meningitis such as *Haemophilus* influenza type b (Hib), Meningitis, viral, meningococcal infections and pneumococcal infection, neglected tropical diseases such as Argentine haemorrhagic fever, Leishmaniasis, Nematode/roundworm infections, Ross river virus infection and West Nile virus (WNV) disease, Non-HIV STDs such as Trichomoniasis, Human papillomavirus (HPV) infections, sexually transmitted chlamydial diseases, Chancroid and Syphilis, Non-septic bacterial infections such as cellulitis, Lyme disease, MRSA infection, *pseudomonas*, staphylococcal infections, Boutonneuse fever, Leptospirosis, Rheumatic fever, Botulism, Rickettsial disease and Mastoiditis, parasitic infections such as Cysticercosis, Echinococcosis, Trematode/Fluke infections, Trichinellosis, Babesiosis, Hypodermyiasis, Diphyllobothriasis and Trypanosomiasis, respiratory infections such as adenovirus infection, aspergillosis infections, Paramyxoviridae (respiratory syncytial virus (RSV), parainfluenza virus (PIV), metapneumovirus (MPV), enteroviruses), Picornaviridae (Rhinovirus, RV), Coronaviridae (CoV), Adenoviridae (Adenovirus), Parvoviridae (HBOV), Orthomyxoviridae (influenza A, B, C, D, Isavirus, Thogotovirus, Quaranjavirus), Herpesviridae (human herpes viruses, Varicella zoster virus, Epstein-Barr virus, cytomegalovirus), avian influenza, smallpox, pandemic influenza, adult respiratory distress syndrome (ARDS) avian (H5N1) influenza, influenza, severe acute respiratory syndrome (SARS), including SARS-COV, Middle East Respiratory Syndrome (MERS-COV), COVID-19 (2019-nCOV, SARS-COV-2), 229E, NL63, OC43, or HKU1, sinusitis, Legionellosis, Coccidioidomycosis and swine (H1N1) influenza, sepsis such as bacteraemia, sepsis/septic shock, sepsis in premature infants, urinary tract infection such as vaginal infections (bacterial), vaginal infections (fungal) and gonococcal infection, viral skin diseases such as B19 parvovirus infections, warts, genital herpes, orofacial herpes, shingles, inner ear infections, fetal cytomegalovirus syndrome, foodborne illnesses such as brucellosis (*Brucella* species), *Clostridium perfringens* (Epsilon toxin), *E. coli* 0157: H7 (*Escherichia coli*), *Salmonellosis* (*Salmonella* species), Shigellosis (*Shigella*), Vibriosis and Listeriosis, bioterrorism and potential epidemic diseases such as Ebola haemorrhagic fever, Lassa fever, Marburg haemorrhagic fever, plague, Anthrax Nipah virus disease, Hanta virus, Smallpox, Glanders (*Burkholderia mallei*), Melioidosis (*Burkholderia pseudomallei*), Psittacosis (*Chlamydia psittaci*), Q fever (*Coxiella burnetii*), Tularemia (*Francisella tularensis*), rubella, mumps, or polio.

SARS-COV-2

As used herein "SARS-COV-2" is a beta-coronavirus (Beta-CoV or β-CoV). In particular, SARS-COV-2 is a Beta-CoV of lineage B. SARS-COV-2 may also be known as 2019 novel coronavirus or "2019-nCOV." The disease associated with SARS-COV-2 is known as COVID-19. Beta-coronaviruses are one of four genera of coronaviruses and are enveloped, positive-sense, single-stranded RNA viruses of zoonotic origin. Beta-coronaviruses mainly infect bats, but they also infect other species like humans, camels, and rabbits. SARS-COV-2 may be transferable between animals, such as between humans. As used herein "viral transmission" is the process by which viruses spread between host subjects. Transmission occurs from person to person by direct or indirect contact or exposure. Examples of direct contact include, but are not limited to, the exchange of body fluids between a subject infected with the virus and another subject. Indirect contact includes, but is not limited to, exposure to bodily fluid droplets produced by a subject infected by the virus during coughing and/or sneezing. Beta-CoVs may induce fever and severe respiratory symptoms in humans.

SARS-COV-2 is the causative agent of the ongoing COVID-19 pandemic. SARS-COV-2 belongs to the family Coronaviridae and is believed to have emerged from the Wuhan, China in the winter of 2019. Since its emergence, SARS-COV-2 has evolved into several widely circulating variants Alpha (B.1.1.7), Beta (B.1.351), Gamma (P.1), and Delta (B.1617.2) and several other variants of lesser concern Epsilon (B.1.427/B.1.429), Zeta (P.2), Eta (B.1.525), Theta (P.3), Iota (B.1.526), and Kappa (B.1617.1). Acute respiratory distress syndrome (ARDS) caused by severe COVID-19 is thought to be fueled by the dramatic elevation of several pro-inflammatory cytokines described as a cytokine storm. IL-10 may play a special role during SARS-COV-2 pathogenesis once it migrates to the lungs where it may help amplify pro-inflammatory mediators and viral sepsis-related hyperinflammation [17-20].

MERS

Middle Eastern Respiratory Syndrome (MERS) is caused by the MERS Coronavirus (MERS-COV) belonging to the family Coronaviridae. First emerging in 2012, the respiratory virus is not as easily transmissible as other respiratory infections, however, it remains a pathogen of high interest. Faure and colleagues described a small case series of two subjects with MERS-CoV infection, in which both subjects demonstrated significant serum expression of CXCL 10 (an epithelial chemokine) and IL-10 in the first week of infection. Interestingly, the subject with a worse outcome demonstrated continued and persistent IL-10 secretion, therefore possibly suppressing a Th-1 response in the host [21].

SARS

Severe acute respiratory syndrome coronavirus (SARS-COV or more recently SARS-COV-1) belongs to the family Coronaviridae and emerged in 2003 in China. While (human) host response to SARS-COV was largely dominated by Th-1 cytokines, several studies demonstrated high serum levels of IL-10 in infected subjects [22-23]. Following natural infection with SARS-CoV, both CD4$^+$ and CD8$^+$ T cells are involved in the immune response to the S, M, E, and N antigens, in which the CD8$^+$ T cells display an effector memory cell phenotype. Conversely, the majority of CD4$^+$ T Cells demonstrated a central memory phenotype. However, the memory Th-1 cells and CD8$^+$ T cells are single-cytokine producing cells, therefore resulting in a diminished effect as antigen-specific neutralizing antibodies [24].

Influenza

Influenza belongs to the family of Orthomyxoviridae and claim four species including the genus Alpha influenzavirus (Influenza A Virus-IAV), Beta influenzavirus (Influenza B virus-IBV), Gamma influenzavirus (Influenza C virus-ICV), Delta influenzavirus (Influenza D virus-IDV. IAV is the causative virus behind many seasonal epidemics and several historical pandemics and attributable to severe illness in humans. IAV can be further classified into subtypes based on the viral proteins hemagglutinin (H) and neuraminidase (N), of which 18 H subtypes and 11 subtypes have been documented in recent history.

Sun and colleagues demonstrated that suppression of IL-10 at the time of Influenza A infection led to the enhanced and localized production of virus-specific antibodies, and therefore increased protection against Influenza A virus infection. Their study demonstrated that mice with IL-10 suppression had improved viral clearance and survival when infected in comparison to the control group [25]. In some instances, subjects with Influenza infection may progress to a secondary infection by pneumococcal pneumonia, which is a serious complication and possibly fatal. In a mouse model, mice were inoculated with infective doses of Influenza A and *S. pneumonia* on day 14. The study demonstrated 50-fold higher pulmonary levels of IL-10 48 hours postsecondary infection, when compared to the control mice. Interestingly, a subgroup of mice was then treated with an anti-IL-10 mAB 1 hour prior to bacterial inoculation. These mice were found to have reduced mortality during the secondary infection [26]. In a more recent animal study, overexpression of IL-10 led to the suppression of invariant natural killer T cells (iNKT), which was associated with susceptibility to pneumococcal superinfection. Neutralization of IL-10 was found to restore iNKT cell activation and resistance to secondary bacterial infections [27].

Ebola

Ebolavirus is a genus of the family Filoviridae that has several subtypes including Zaire Ebolavirus (known as Ebola Virus), Sudan Ebolavirus, Bundibugyo ebolavirus, Taï Forest Ebolavirus, and Reston Ebolavirus infecting both human and non-human primates. Infection by Ebola Virus may induce an acute hemorrhagic fever known as Ebola Virus Disease (EVD). EVD has a mortality rate anywhere form 40-80%. In a study comparing inflammatory responses between non-survivors and survivors of Ebola virus disease, those with fatal infections had significant plasma levels of IL-10 [12]. This was consistent with another study in an earlier Ebola outbreak in Kikwit, which also demonstrated that fatal Ebola infections were associated with high levels of IL-10, as well as IFN-$\alpha$, interleukin, (IL)-2, and INF-$\gamma$ [12]. Both studies demonstrated weak levels of IL-1$\beta$, IL-6, MIP-1B, and TNF-$\alpha$, which may have been suppressed by the high levels of IL-10 [12, 28, 29]. A more recent study found that IL-10 overexpression continued until fatality, with a correlation between levels and days since infection [28].

Tuberculosis

Tuberculosis (TS) is largely caused by the bacterium *Mycobacterium tuberculosis* (MTB), while other possible mycobacteria include *M. bovis, M. africanum, M. canetti,* and *M. microti*. The only approved vaccine against TB is Bacille Clamette-Guerin (BCG), however, the efficacy of BCG in its protection against TB infection varies among populations. A mice model in IL-10 deficient mice showed a significantly superior uptake of the BCG vaccine in comparison to a control group (wild type mice). The study demonstrated that IL-10 prevents the activation of dendritic cells (DC) which are activated by the BCG vaccine but are suppressed by the upregulation of IL-10. Secondly, "educated" DCs interact with CD4$^+$ T cells which boost BCG vaccine efficacy in the mice model [30].

Leishmaniasis

Leishmaniasis and its clinical subtypes (i.e., cutaneous, mucocutaneous, and/or visceral Leishmaniasis) are caused by the parasites of the trypanosome genus *Leishmania*. The disease currently effects anywhere from 4 to 12 million people and more than 20 species of *Leishmania* can be responsible for human infection. Various vaccines are in development to protect against Leishmaniasis. Stober and colleagues described how IL-10 inhibition greatly boosted vaccine efficacy *Leishmania major*-infected mice. Specifically, IL-10 was responsible for vaccine failure in mice and IL-10 levels relative to IFN-$\gamma$ provided the best pre-challenge predictor of vaccine efficacy [31].

Design, Synthesis, and Production

The solid phase synthesis of a cDNA can be acquired from a number of commercial vendors. The synthesized cDNA is inserted or lighted into a commercially available bacterial plasmid (pDNA) that contains an origin of replication, antibiotic selectable resistance genes, and bacteriophage T7 polymerase (or any bacteriophage RNA transcription polymerase such as T3 for SP6). The pDNA is used to transform competent bacterium grown in an appropriate antibiotic to select for a pDNA transformed bacteria that will allow growth and amplification of the pDNA. The manufactured pDNA can be retrieved from the bacteria by lysis of the bacteria and separation of pDNA from the bacterial chromosomal DNA by centrifugation and ethanol precipitation.

The closed circular pDNA is linearized using a commercially available restriction endonuclease that allows separation of the linear form from other DNA by size exclusion chromatography. In vitro transcription of mRNA from the T7 polymerase includes nucleotide triphosphates (NTP) and a 5'-cap can be added. The 5'-cap is an option since the vaccine has an internal ribosomal entry site (IRES) in the 5'-untranslated region (5'-UTR). Extraction and precipitation steps remove unincorporated NTP and NTP metabolites, but some incomplete or shorter RNA will remain. Size exclusion chromatography separates mRNA based on size and it will remove shorter incomplete mRNA as well as contaminating double stranded RNA (dsRNA). Removal of dsRNA that may form is key in that it can stimulate unwanted innate immune responses. These processing steps are currently available at commercial GMP facilities that will ensure FDA compliant substance for human clinical use.

Modifications

The oligonucleotide modifications support Watson-Crick pairing to standard polynucleotide bases. The modified oligonucleotide backbone presents bases in a manner to permit hydrogen bonding in a sequence-specific manner between the oligonucleotide analog molecule and the bases in a standard polynucleotide, such as single-stranded RNA. In one embodiment the analog has an uncharged phosphorus containing backbone. Non-ionic oligonucleotide analogs, i.e., oligomers having backbones include phosphotriester-linked, methylphosphonate-linked, carbamate, phosphorodiamidate morpholino (PMO), dimethylamino-linked, and peptide nucleic acids (PNA).

In one embodiment, the modified oligonucleotide includes a nuclease resistant backbone that is not susceptible to nuclease cleavage. Nuclease-resistant oligonucleotides may have charged (polyanionic or polycationic) or uncharged backbones. Polyanionic includes phosphorothioate, bromophosphonate, phosphorodithioate, and phosphate amine DNA. Neutral (uncharged) backbones include phosphorodiamidate morpholino (PMO), dimethylamine-linked phosphate, or methylphosphonate. See US20110318382 A1 which is incorporated by reference herein for such teachings.

In one embodiment, the modified oligomer structure includes a uniformly modified 2'-O-methyl ribose sugar backbone, dimethylamino-linked phosphate linkages, and standard pyrimidine and purine base pairing moieties typically including adenine, cytosine, guanine, thymine, uracil, and inosine. For example, one embodiment described herein is an antisense oligonucleotide such as SEQ ID NO: 1-11, wherein each nucleotide contains a 2'-O-methyl, 2'-O-ethyl, or 2'-methoxyethyl moeity on the 2'-hydroxyl. In another embodiment, the antisense oligonucleotide such as SEQ ID NO: 1-11 contains uniform replacement of the ribose sugar with a morpholino subunit and phosphorous-containing intersubunit linkages (PMO), dimethylamine-linked phosphate, or methylphosphonate.

Pharmaceutical Vaccine Compositions

The compositions of the vaccine adjuvant include four CpG sequences within the hCG mRNA (SEQ ID NO: 5) known to stimulate innate immune surveillance pathways through toll-like receptors. In addition, an antisense oligonucleotide designed to bind near the splice acceptor region of exon 4 of interleukin 10 capable of inhibiting the expression of IL-10.

IL-10 is an anti-inflammatory glycoprotein that participates in the regulation of immunity. IL-10 inhibits the activity of Th1 cells (a sub population of CD4$^+$ T-cells), natural killer T-cells (NK), and macrophages that contribute to clearance of tumor tissue and infected cells. Expression and secretion of IL-10 inhibits the synthesis of interferon gamma (IFN-$\gamma$), IL-2, IL-3, tumor necrosis factor (TNF), and GM-CSF produced by activated macrophages and helper T-cells resulting in the inhibition of immune responses participating in clearance of tumor cells. Several immune cell type express IL-10 including macrophages, dendritic cells, B-cells, and subsets of CD4$^+$ and CD8$^+$ T-cells.

An antisense oligonucleotide designed to bind to the splice acceptor region of exon four of IL-10 pre-mRNA (sequence 5'-GGAGAAATCGATGCTGAAGAA-3'; IL-10E4SA; SEQ ID NO: 1) led to skipping of exon 4 in the mature mRNA and reduced translation to the IL-10 protein. The IL10E4SA was determined to be optimal in targeting a variety of IL-10 transcript sites [1]. The inhibition of IL-10 protein in freshly isolated bone-marrow derived cells cultured to promote differentiation into dendritic cells was sequence specific, dose, and time dependent. When administered to mice that were challenged with a lethal mouse adapted Ebola virus, a survival benefit was observed in 7 replicate experiments of 10 mice in each treatment group for a cumulative of 41 survivors in the 70 infected mice compared to less than 10 survivors in 70 infected mice in vehicle control groups. Antibody depletion studies in IL-10$^{-/-}$ mice suggest a role for NK cells and IFN-gamma for the improved immune response in clearing infected cells. The capacity to shift Th1/Th2 balance with IL-10E4SA antisense oligomers represents a unique adjuvant strategy for vaccines to immunize against infectious diseases or pathogens of interest.

Pharmaceutical Formulations

Intravenous Injections

Phosphate buffered saline (PBS) containing inactive ingredients-potassium phosphate mono basic, anhydrous, USP; potassium chloride, USP; sodium phosphate diabetic, anhydrous, USP; sodium chloride, USP; and water for injection, USP. Active ingredients include mRNA with and without antisense IL-10E4SA. The phosphate buffered saline with and without enhanced delivery agents including lipid nanoparticles (LNP) including but not limited to lipids (including ((4-hydroxybutyl)azanediyl)bis(hexane-6,1-diyl) bis(2-hexyldecanoate), 2 [(polyethylene glycol)-2000]-N,N-ditetradecylacetamide, 1,2-distearoyl-sn-glycero-3-phosphocholine, and cholesterol), perflourocarbon micro bubbles (C4F10 or C5F12), or cationic peptides including but not limited to ArgArgArgArgArgArgGly (R$_6$G) (SEQ ID NO: 12).

Intramuscular Injections

A PBS solution as described for intravenous injection including mRNA with and without antisense IL-10E4SA administered in a solution of less than one milliliter into a muscle, e.g., the shoulder. The PBS solution with or without enhanced delivery agents including lipid nanoparticles (LNP) or cationic peptides including but not limited to R$_6$G (SEQ ID NO: 12).

Inhalation/Insufflation

A PBS solution as described for intravenous injection including mRNA with and without antisense IL-10E4SA administered by an aerosol spray delivery device intranasally.

A dry powder composed of aerodynamic particle size distribution—a fine particle fraction (FPF) greater than 50 percent, a mean mass aerodynamic diameter (MMAD) of 2.0-2.5 micrometers, emitted dose (ED) of greater than 35 percent neat mRNA with and without IL-10E4SA and salt. The dry powder will be delivered by a flow-controlled inhalation metered device.

Oral

An oral rehydration solution (ORT) composed of 2.6 g NaCl, 2.9 g trisodium citrate, 1.5 g potassium chloride, 13.5 g anhydrous glucose, and mRNA with and without antisense IL-10E4SA in one liter of water.

An oral solid dosage (pills or capsules) containing mRNA with or without antisense IL-10E4SA and excipients including binders, glidants, disintegrants, and lubricants to facilitate fill formation and dissolution in the gut.

Formulations, Administration, Delivery, and Dosing

Formulations

The adjuvant can be formulated by multiple strategies as described herein. Subjects seeking vaccination will have confirmed disease and will be screened for prior adverse reactions to vaccines to exclude subjects that may experience serious adverse reactions. No concurrent chemotherapy is permitted due to likelihood of immune suppressive actions of chemotherapy that may limit the efficacy of an hCG mRNA vaccine. Both male and female subjects of all ethnic and ideological groups are included. Female subjects of childbearing age are advised that the vaccination will prevent pregnancy.

Administration

The vaccine adjuvant is administered by applicable routes of administration such as an oral route, intramuscular injection, or by inhalation/insufflation, with doses ranging from 0.03 mg to 0.10 mg. The adjuvant is administered on a schedule consistent with the vaccine. Subjects are monitored for disease progression by standard procedures under the care of a qualified clinician.

Delivery Methods

Direct pulmonary delivery (e.g., aerosol, inhalers, etc.) is a more selective mode of drug delivery that typically requires a lower quantity of drug. However, direct pulmonary delivery can have limited efficacy due to improper dosing, stability issues, and difficulty in producing an optimum particle size. Pulmonary drug delivery can provide the following advantages: quick onset of action coupled with ease and convenience of administration; the pulmonary dose is significantly lower than the oral dose; and degradation of the drug in the liver can be avoided. On the other hand, the following drawbacks are often associated with pulmonary drug delivery: improper dosing; stability problems; and difficulty in producing the optimum particle size. In addition, not all drugs can be delivered via a pulmonary route due to formulation difficulties.

Local adjuvant administration can be buttressed by using different types of drug delivery vehicles (nanoparticle drug carriers, liposomes, viral vectors, or microbubbles). The latter adhere to sites of damaged vascular endothelium and thus may be a method of systemically targeting delivery of therapeutics to damaged organ. For example, perfluorobutane gas microbubbles with a coating of dextrose and albumin efficiently bind to different pharmaceuticals. These 0.3-10.0 μm particles bind to sites of vascular injury. Further, the perfluorobutane gas is an effective cell membrane fluidizer. The potential advantages of microbubble carrier delivery include none to minimal (additional) vessel injury through delivery, no resident polymer to degrade and lead to eventual inflammation, rapid bolus delivery, and repeated delivery. Microbubble carriers were successfully used in different animal models and clinical trials to deliver antisense oligonucleotide and/or Sirolimus to the injured vascular bed.

Extracellular Vesicles (EV)

Kumar and colleagues describe the use of extracellular vesicles (EVs), which are a family of natural carriers in the human body. EVs play a critical role in cell-to-cell communications and can be used as unique drug carriers of therapeutic vaccine to tumors. Though the authors of the reported investigations concluded that certain limitations need to be overcome as well as understanding the mechanism to control targeted delivery. Specifically, the isolation and drug encapsulation techniques employed to engineer EVs could result in the loss of functional properties of the EVs, such as the destruction of surface proteins. These unintended changes could lead to nonspecific interactions with other cells, leading to off-target effects, toxicity, and suboptimal efficacy.

Adenosine Nanoparticles

Recently, the efficacy in mitigating inflammation was demonstrated through the targeted delivery of adenosine and of multi-drug formulations. Bioconjugation of adenosine to squalene produces a prodrug-based nanocarrier, which, after nano formulation with Vit E, yields stable multidrug nanoparticles. This nanoparticle improves the bioavailability of both drugs with significant pharmaceutical activity in models of acute inflammatory injury.

Novel Bio-Objects

A group of researchers has succeeded in engineering a new kind of microscopic bio-object that may one day be used for personalized diagnostics and targeted delivery of drugs. The object consists of a genetically modified *E. coli* bacterium and nano-erythrocytes (small vesicles made of red blood cells), and it demonstrates a substantial improvement in motility over previous designs.

Nanobodies

In some embodiments a therapeutic vaccine can be delivered using nanobodies. Indeed, several researchers have shown that nanobodies, which are tiny immune proteins, can enhance site specific delivery and residence of vaccines.

Nanomicelles

In brain tumors vaccine may be delivered brain-derived neurotrophic factor mRNA using polyplex nanomicelle.

Ischemic neuronal death causes serious lifelong neurological deficits; however, there is no proven effective treatment that can prevent neuronal death after the ischemia. We investigated the feasibility of mRNA therapeutics for preventing the neuronal death in a rat model of transient global ischemia (TGI). By intraventricular administration of mRNA encoding brain-derived neurotrophic factor (BDNF) using a polymer-based carrier, polyplex nanomicelle, the mRNA significantly increased the survival rate of hippocampal neurons after TGI, with a rapid rise of BDNF in the hippocampus.

The nanomicelle has a core-shell structure surrounded by a PEG outer shell and an mRNA-containing core for stable retention of the mRNA in the nanomicelle. The local administration of mRNA loaded nanomicelles has already shown therapeutic potential in various organs, such as the liver, joint cartilage, intervertebral disks, and the neural tissues, including the brain. Nanomicelles can also block the immune responses to extracellular mRNA by shielding them from recognition by the toll-like receptors in target cells.

Alternatively, different carriers such as micro-particles, nanoparticles, injectable polymers or natural carriers and others may be used to enhance penetration and residence of therapeutics at the target area.

Other examples include silicon-based hydrogels; PEG-based polymers; nanoparticle-containing hydrogels; hydrogels containing cyclodextrins (CDs); hydrophilic polymers or poly ethylene glycol (PEG) provides water solubility to hydrogels, other polymers like as poly lactic acid (PLA), poly ε-caprolactone (PCL), polypropylene oxide (PPO), poly D,L-lactide-co-glycolide (PLGA) and poly ε-caprolactone-co-D,L-lactide (PCLA); ultra-thermosensitive hydrogel; hydrogels with different systems, namely, emulsions, vesicular (including micelles, liposomes and nanocapsules)

and particulate systems (including mainly solid lipid micro and nanoparticles, nanostructured lipid carriers and lipid drug conjugates); biocompatible hydrogel, composed of the copolymer poly(N-isopropylamide-co-n-butyl methacrylate) [poly(IPAAm-co-BMA)] and PEG; A polyethylenimine (PEI)-based hydrogel; supramolecular hydrogels; DNA-hydrogels; bioinspired hydrogels; and multi-functional and stimuli-responsive hydrogels; n-acrylic polymer impregnated with porcine gelatin; and gelatin.

To avoid the disadvantages of oral or direct injection administration of drugs, a number of modes of administration of continuous dose, long-term delivery devices include reservoir devices, osmotic devices, and pulsatile devices for delivering beneficial agents have been utilized. Injecting drug delivery systems as small particles, microparticles or microcapsules avoids the incision needed to implant drug delivery systems. Microparticles, microspheres, and microcapsules, referred to herein collectively as "microparticles", are solid or semi-solid particles having a diameter of less than one millimeter, more preferably less than 100 microns, which can be formed of a variety of materials, including synthetic polymers, and proteins. Another intensively studied polymeric injectable depot system is an in situ-forming implant system. In situ-forming implant systems are made of biodegradable products, which can be injected via a syringe into the body, and once injected, congeal to form a solid biodegradable implant.

Dosing

In one embodiment, the pharmaceutical compositions described herein provide a dosage form of the pharmaceutical compositions described here for administration to a subject. The dosage form can be administered, for example, to a subject, or a subject in need thereof. In one aspect, the subject is a mammal, or a mammal in need thereof. In one aspect, the subject is a human, or human in need thereof. In one aspect, the subject is a human or a human in need thereof. In one aspect, the subject is a child (~0-9 years old) or an adolescent (~10-17 years old). In one aspect, the subject is from about 0 to about 9 years of age. In another aspect, the subject is from about 10 years to about 17 years of age. In another aspect, the subject is over 17 years of age. In another aspect, the subject is an adult ($\geq$18 years of age).

Administration can be by any appropriate route, including injection or intranasal (insufflation).

The dosing of the adjuvant vaccine may range from 0.01 mg to 10 mg, including all integers within the range. In one aspect, the dose is 0.03 mg to 0.10 mg, including all integers within the range. In one aspect, the dose is 0.03, 0.04, 0.05, 0.06, 0.07, 0.08, 0.09, or 0.10 mg.

It will be apparent to one of ordinary skill in the relevant art that suitable modifications and adaptations to the compositions, formulations, methods, processes, apparatuses, assemblies, and applications described herein can be made without departing from the scope of any embodiments or aspects thereof. The compositions, apparatuses, assemblies, and methods provided are exemplary and are not intended to limit the scope of any of the disclosed embodiments. All the various embodiments, aspects, and options disclosed herein can be combined in any variations or iterations. The scope of the compositions, formulations, methods, apparatuses, assemblies, and processes described herein include all actual or potential combinations of embodiments, aspects, options, examples, and preferences described herein. The compositions, formulations, apparatuses, assemblies, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

Various embodiments and aspects of the inventions described herein are summarized by the following clauses:

Clause 1. An antisense inhibitor adjuvant composition comprising a nucleotide sequence complementary to a *Homo sapiens* interleukin 10 (IL-10) or interleukin 10 receptor alpha (IL-10RA) gene, wherein the nucleotide sequence comprises one or more of:

(i) uniform modifications of each nucleotide with 2'-O-methyl, 2'-O-ethyl, or 2'-methoxyethyl substituents or uniform replacement of the ribose sugar with a morpholino subunit and phosphorous-containing intersubunit linkages, (PMO), dimethylamine-linked phosphate, or methylphosphonate;

(ii) a free energy ($\Delta G$) of hybridization of −25 to −35 kcal/mol; and (iii) a single mismatch ("blebmer") with a target RNA to enhance the steric blocking of RNA function.

Clause 2. The composition of clause 1, wherein the nucleotide sequence comprises a nucleic acid sequence with at least 90-99% identity to SEQ ID NO: 1-11.

Clause 3. The composition of clause 1, wherein the nucleotide sequence comprises SEQ ID NO: 1-11.

Clause 4. The composition of clause 1, further comprising one or more aminoglycosides.

Clause 5. The composition of clause 4, wherein the aminoglycoside comprises one or more of Kanamycin A, Amikacin, Tobramycin, Dibekacin, Gentamicin, Sisomicin, Netilmicin, Neomycin B, Neomycin C, Neomycin E (paromomycin), Streptomycin, Plazomicin, or Neo-Fradin.

Clause 6. A method for suppressing an IL-10 immune response associated with a vaccine, the method comprising administering an antisense inhibitor adjuvant comprising an antisense inhibitor adjuvant composition of clause 1.

Clause 7. The method of clause 6, wherein the vaccine is for an infectious disease selected from one or more of Herpes simplex, type 1; Herpes simplex, type 2; encephalitis virus, papillomavirus, Varicella-zoster virus; Epstein-Barr virus; Human cytomegalovirus; Human herpesvirus, type 8; Human papillomavirus; BK virus; JC virus; Smallpox; polio virus, Hepatitis B virus; Human bocavirus; Parvovirus B19; Human astrovirus; Norwalk virus; coxsackievirus; hepatitis A virus; poliovirus; rhinovirus; Hepatitis C virus; yellow fever virus; dengue virus; West Nile virus; Rubella virus; Hepatitis E virus; Human immunodeficiency virus (HIV); Influenza virus, type A or B; Guanarito virus; Junin virus; Lassa virus; Machupo virus; Sabiá-virus; Crimean-Congo hemorrhagic fever virus; Ebola virus; Marburg virus; Measles virus; Mumps virus; Parainfluenza virus; Respiratory syncytial virus; Human metapneumovirus; Hendra virus; Nipah virus; Rabies virus; Hepatitis D; Rotavirus; Orbivirus; Coltivirus; Hantavirus; Coronavirus, including SARS-CoV-2, Severe acute respiratory syndrome virus, and Middle East Respiratory Coronavirus; Chikungunya virus, Banna virus, Tuberculosis, or Leishmaniasis.

Clause 8. The method of clause 6 or 7, wherein the vaccine is for SARS-COV-2, Severe acute respiratory syndrome virus, Middle East Respiratory Coronavirus, Dengue, Influenza, Ebola, Tuberculosis, or Leishmaniasis.

Clause 9. The method of any one of clauses 6-8, wherein the adjuvant is administered prior to, concurrently with, or following administration of a vaccine.

Clause 10. The method of any one of clauses 6-9, wherein the adjuvant is administered orally, by injection, or by inhalation/insufflation.

Clause 11. The method of any one of clauses 6-10, wherein the adjuvant is administered with one or more second adjuvants.

Clause 12. The method of clause 11, wherein the second adjuvant comprises one or more of: cationic liposome-DNA complex JVRS-100, aluminum hydroxide vaccine adjuvant, aluminum phosphate vaccine adjuvant, aluminum potassium sulfate adjuvant, ALHDRO-GEL™, ISCOM(s)™, Freund's Complete Adjuvant, Freund's Incomplete Adjuvant, CpG DNA Vaccine Adjuvant, Cholera toxin, Cholera toxin B subunit, Liposomes, Saponin Vaccine Adjuvant, DDA Adjuvant, Squalene-based Adjuvants, Etx B subunit Adjuvant, IL-12 Vaccine Adjuvant, LTK63 Vaccine Mutant Adjuvant, TITERMAX™ Gold Adjuvant, Ribi Vaccine Adjuvant, Montanide ISA 720 Adjuvant, *Corynebacterium*-derived P40 Vaccine Adjuvant, MPL™ Adjuvant, AS04, AS02, Lipopolysaccharide Vaccine Adjuvant, Muramyl Dipeptide Adjuvant, CRL1005, Killed *Corynebacterium parvum* Vaccine Adjuvant, Montanide ISA 51, *Bordetella pertussis* component Vaccine Adjuvant, Cationic Liposomal Vaccine Adjuvant, Adamantylamide Dipeptide Vaccine Adjuvant, Arlacel A, VSA-3 Adjuvant, Aluminum vaccine adjuvant, Polygen Vaccine Adjuvant, ADJUMER™, Algal Glucan, Bay R1005, THERAMIDER, Stearyl Tyrosine, Specol, Algammulin, AVIRDINE®, Calcium Phosphate Gel, CTA1-DD gene fusion protein, DOC/Alum Complex, Gamma Inulin, Gerbu Adjuvant, GM-CSF, GMDP, Recombinant hIFN-γ, interferon-γ, Interleukin-1β, Interleukin-2, Interleukin-7, Sclavo peptide, REHYDRAGEL™ LV, REHYDRAGEL™ HPA, Loxoribine, MF59, MTP-PE Liposomes, Murametide, Murapalmitine, D-Murapalmitine, NAGO, Non-Ionic Surfactant Vesicles, PMMA, Protein Cochleates, QS-21, SPT (Antigen Formulation), nanoemulsion vaccine adjuvant, AS03, QUIL-AR vaccine adjuvant, RC529 vaccine adjuvant, LTR 192G Vaccine Adjuvant, *E. coli* heat-labile toxin, LT, amorphous aluminum hydroxyphosphate sulfate adjuvant, Calcium phosphate vaccine adjuvant, Montanide Incomplete Seppic Adjuvant, Imiquimod, Resiquimod, AF03, Flagellin, Poly(I:C), ISCOMATRIX®, Abisco-100 vaccine adjuvant, Albumin-heparin microparticles vaccine adjuvant, AS-2 vaccine adjuvant, B7-2 vaccine adjuvant, DHEA vaccine adjuvant, Immunoliposomes Containing Antibodies to Costimulatory Molecules, SAF-1, Sendai Proteoliposomes, Sendai-containing Lipid Matrices, Threonyl muramyl dipeptide (TMDP), Ty Particles vaccine adjuvant, Bupivacaine vaccine adjuvant, D,L-PGL (Polyester poly (D,L-lactide-co-glycolide)) vaccine adjuvant, IL-15 vaccine adjuvant, TK72 vaccine adjuvant, MPL-SE vaccine adjuvant, non-toxic mutant E112K of Cholera Toxin mCT-E112K, and/or Matrix-S.

Clause 13. The method of any one of clauses 6-12, wherein the adjuvant is administered with one or more aminoglycosides.

Clause 14. The method of clauses 13, wherein the aminoglycoside comprises one or more of Kanamycin A, Amikacin, Tobramycin, Dibekacin, Gentamicin, Sisomicin, Netilmicin, Neomycin B, Neomycin C, Neomycin E (paromomycin), Streptomycin, Plazomicin, or Neo-Fradin.

Clause 15. A method for suppressing an IL-10 immune response as a treatment of a viral, bacterial, or other pathogen infection, comprising administering the antisense inhibitor composition of clause 1.

Clause 16. The method of clause 15, wherein the viral, bacterial, or other pathogen infection is selected from one or more of Herpes simplex, type 1; Herpes simplex, type 2; encephalitis virus, papillomavirus, Varicella-zoster virus; Epstein-barr virus; Human cytomegalovirus; Human herpesvirus, type 8; Human papillomavirus; BK virus; JC virus; Smallpox; polio virus, Hepatitis B virus; Human bocavirus; Parvovirus B19; Human astrovirus; Norwalk virus; coxsackievirus; hepatitis A virus; poliovirus; rhinovirus; Hepatitis C virus; yellow fever virus; dengue virus; West Nile virus; Rubella virus; Hepatitis E virus; Human immunodeficiency virus (HIV); Influenza virus, type A or B; Guanarito virus; Junin virus; Lassa virus; Machupo virus; Sabiávirus; Crimean-Congo hemorrhagic fever virus; Ebola virus; Marburg virus; Measles virus; Mumps virus; Parainfluenza virus; Respiratory syncytial virus; Human metapneumovirus; Hendra virus; Nipah virus; Rabies virus; Hepatitis D; Rotavirus; Orbivirus; Coltivirus; Hantavirus; Coronavirus, including SARS-CoV-2, Severe acute respiratory syndrome virus, and Middle East Respiratory Coronavirus; Chikungunya virus, Banna virus, Tuberculosis, or Leishmaniasis.

Clause 17. The method of clause 15 or 16, wherein the viral, bacterial, or other pathogen infection is selected from SARS-COV-2, Severe Acute Respiratory Syndrome virus, Middle East Respiratory Coronavirus, Dengue, Influenza, Ebola, Tuberculosis, or Leishmaniasis.

Clause 18. The method of any one of clauses 15-17, wherein the antisense inhibitor is administered with one or more therapeutics.

Clause 19. The method of any one of clause 15-18, wherein the antisense inhibitor is administered prior to, concurrently with, or following administration of a therapeutic.

Clause 20. The method of any one of clauses 15-19, wherein the antisense inhibitor is administered orally, by injection, or by inhalation/insufflation.

Clause 21. The method of any one of clauses 15-20, wherein the antisense inhibitor is administered with one or more aminoglycosides.

Clause 22. The method of clauses 21, wherein the aminoglycoside comprises one or more of Kanamycin A, Amikacin, Tobramycin, Dibekacin, Gentamicin, Sisomicin, Netilmicin, Neomycin B, Neomycin C, Neomycin E (paromomycin), Streptomycin, Plazomicin, or Neo-Fradin.

REFERENCES

1. Panchal et al., "Induced IL-10 splice altering approach to antiviral drug discovery," *Nucleic Acid Ther.* 24 (3): 179-185 (2014).

2. Clerici et al., "Role of interleukin-10 in T helper cell dysfunction in asymptomatic individuals infected with the human immunodeficiency virus," *J. Clin. Invest.* 93 (2): 768-775 (1994).

3. Rico et al., "Hepatitis B virus-specific T-cell proliferation and cytokine secretion in chronic hepatitis B e antibody-positive patients treated with ribavirin and interferon alpha," *Hepatology* 33 (1): 295-300 (2001).

4. Brady et al., "Hepatitis C virus non-structural protein 4 suppresses Th1 responses by stimulating IL-10 production from monocytes," *Eur. J. Immunol.* 33 (12): 3448-3457 (2003).

5. Klenerman and Hill, "T cells and viral persistence: lessons from diverse infections," *Nat. Immunol.* 6 (9): 873-879 (2005).

6. Brooks et al., "Interleukin-10 determines viral clearance or persistence in vivo," *Nat. Med.* 12 (11): 1301-1309 (2006).

7. Landay et al., "In vitro restoration of T cell immune function in human immunodeficiency virus-positive persons: effects of interleukin (IL)-12 and anti-IL-10," *J. Infect. Dis.* 173 (5): 1085-1091 (1996).

8. Autran, et al., "Therapeutic vaccines for chronic infections," *Science* 305 (5681): 205-208 (2004).

9. Brooks et al., "IL-10 blockade facilitates DNA vaccine-induced T cell responses and enhances clearance of persistent virus infection," *J. Exp. Med.* 205 (3): 533-541 (2008).

10. Mohanty et al., "Prolonged proinflammatory cytokine production in monocytes modulated by interleukin 10 after influenza vaccination in older adults," *J. Infect. Dis.* 211 (7): 1174-1184 (2015).

11. Adikari et al., "Dengue NS1 antigen contributes to disease severity by inducing interleukin (IL)-10 by monocytes," *Clin. Exp. Immunol.* 184 (1): 90-100 (2016).

12. Baize et al., "Inflammatory responses in Ebola virus-infected patients," *Clin. Exp. Immunol.* 128 (1): 163-168 (2002).

13. Kwilasz, et al., "The therapeutic potential of interleukin-10 in neuroimmune diseases," *Neuropharmacology* 96 (Pt A): 55-69 (2015).

14. Abers et al., "An immune-based biomarker signature is associated with mortality in COVID-19 patients," *JCI Insight* 6 (1): e144455 (2021).

15. Dhar et al., "IL-6 and IL-10 as predictors of disease severity in COVID-19 patients: results from meta-analysis and regression," *Heliyon* 7 (2): e06155 (2021).

16. Diao et al., "Reduction and Functional Exhaustion of T Cells in Patients With Coronavirus Disease 2019 (COVID-19)," *Front. Immunol.* 11:827 (2020).

17. Luo et al., "Interleukin-10 inhibits *Mycobacterium bovis bacillus* Calmette-Guerin (BCG)-induced macrophage cytotoxicity against bladder cancer cells," *Clin. Exp. Immunol.* 160 (3): 359-368 (2010).

18. Li et al., "SARS-COV-2 and viral sepsis: observations and hypotheses," *Lancet* 395 (10235): 1517-1520 (2020).

19. Lu, et al., "A Potential Role of Interleukin 10 in COVID-19 Pathogenesis," *Trends Immunol.* 42 (1): 3-5 (2021).

20. Xu et al., "Pathological findings of COVID-19 associated with acute respiratory distress syndrome," *Lancet Respir. Med.* 8 (4): 420-422 (2020).

21. Faure et al., "Distinct immune response in two MERS-COV-infected patients: can we go from bench to bedside?" *PLOS One* 9 (2): e88716 (2014).

22. Li et al., "The relationship between serum interleukins and T-lymphocyte subsets in patients with severe acute respiratory syndrome," *China Med. J.* (Engl) 116 (7): 981-984 (2003).

23. Zhu, "SARS Immunity and Vaccination," *Cell. Mol. Immunol.* 1 (3): 193-198 (2004).

24. Fan et al., "Characterization of SARS-COV-specific memory T cells from recovered individuals 4 years after infection," *Arch. Virol.* 154 (7): 1093-1099 (2009).

25. Sun et al., "A detrimental effect of interleukin-10 on protective pulmonary humoral immunity during primary influenza A virus infection," *J. Virol.* 84 (10): 5007-5014 (2010).

26. van der Sluijs et al., "IL-10 is an important mediator of the enhanced susceptibility to pneumococcal pneumonia after influenza infection," *J. Immunol.* 172 (12): 7603-7609 (2004).

27. Barthelemy et al., "Influenza A virus-induced release of interleukin-10 inhibits the anti-microbial activities of invariant natural killer T cells during invasive pneumococcal superinfection," *Mucosal. Immunol.* 10 (2): 460-469 (2017).

28. Reynard et al., "Immune parameters and outcomes during Ebola virus disease," *JCI Insight* 4 (1): e125106 (2019).

29. Villinger et al., "Markedly elevated levels of interferon (IFN)-gamma, IFN-alpha, interleukin (IL)-2, IL-10, and tumor necrosis factor-alpha associated with fatal Ebola virus infection," *J. Infect. Dis.* 179 Suppl 1: S188-S191 (1999).

30. Xu et al., "IL-10 Dampens the Th1 and Tc Activation through Modulating DC Functions in BCG Vaccination," *Mediators Inflamm.* 2019:8616154 (2019).

31. Stober et al., "IL-10 from regulatory T cells determines vaccine efficacy in murine *Leishmania major* infection," *J. Immunol.* 175 (4): 2517-2524 (2005).

EXAMPLES

Example 1

Enhanced CD8 Response to Lysteria Infection

A murine antisense oligonucleotide (SEQ ID NO: 5) composed of a cell-penetrating peptide conjugated phosphonodiamidite morpholino chemistry was administered to mice daily at a dose of 0.2 mg/mouse/day (50 mg/kg/day) for two consecutive days by intraperitoneal injection (IP). The oligomer was conjugated at the 5'-end with a cell penetrating peptide, NH$_2$-RXRRXRRXRRXRXB—COOH, (RXR)$_4$XB, (SEQ ID NO: 17) where R indicates arginine, X indicates 6-aminohexanoic acid, and B indicates β-alanine (referred to as "P007"-SEQ ID NO: 36 in U.S. Pat. App. Pub. No. US20110318382 A1). Earlier studies confirmed this dose of IL-10 antisense suppress expression of IL-10. The experimental design involved two groups of 4 mice per group: a control and an IL-10 antisense group. Both groups were infected with a sublethal challenge of Lysteria *monocytogenes*. The experiment included CD8 T-cell responses to Lysteria antigen which was significantly greater in mice treated with IL-10 antisense compared the control mice. The observations confirm transient suppression of IL-10 leads to a shifting of immune responses toward CD8 bacterial clearance.

Example 2

Antisense IL-10 as a DNA Vaccine Adjuvant

Three groups of C57BL mice: (1) a control group of mice that did not receive vaccine or IL-10 antisense (SEQ ID NO: 3), (2) a DNA vaccine encoding ovalbumin administered on days 0, 6, and 11 by the IP route, and (3) a DNA vaccine as in group 2 plus 0.05 mg and a phosphorodiamidate morpholino oligomer antisense to IL-10 (SEQ ID NO: 3) also on a schedule of day 0, 6, and 11 also by the IP route. The experiment was terminated on day 15 and splenocytes and lymph nodes were harvested, and a cell suspension was prepared. CD8 T-cells were incubated in the yellow fluorescent dye, CFSE, and then the ovalbumin antigen plus IL-2. The CFSE signal was measured by flow cytometry. Only cells recovered from the DNA vaccine and IL-10 antisense showed greater than 10-fold dilution of the CFSE dye indicating T-cell proliferation in response to antigen. The cells were also evaluated by flow cytometry in which a marker of CD8 cell number versus SIINFKL tetramer binding (a marker of ovalbumin T-cell response) revealed 4% positive cells in the antisense treated group versus 1.3% positive in the vaccine only group. Cells were also evaluated for IFNγ versus TNFα positivity, demonstrating a 3-fold increase (1% in antisense treated versus 0.3% in vaccine only) in cells positive for both markers in the antisense treated group. These observations are consistent with the transient inhibition of IL-10 leading to an augmented CD8 T-cell response to antigen.

Example 3

Augmenting *Bacillus* Calmette-Guerin (BCG) Vaccination for Bladder Cancer by Inhibiting IL-10

Peritoneal macrophages were harvested after stimulation with thioglycollate and then stimulated with BCG for 24 hours. The cells were incubated with 51Cr-labeled MBT-2 (murine bladder cancer cells) target cells. An IL-10 neutralizing antibody was added to test samples and 51Cr release measured as a marker of CTL activity. A ratio of effector to target cells of 10:1 was associated with more than 50 times greater target cell lysis when IL-10 was neutralized with antibody compared to no suppression of IL-10 [17].

What is claimed:

1. An adjuvant composition comprising:

one or more antisense nucleotide sequences complementary to a human interleukin 10 mRNA having a single mismatch and selected from SEQ ID NO: 2-6; or one or more antisense nucleotide sequences complementary to a human interleukin 10 receptor alpha mRNA comprising nucleotides having a single mismatch and selected from SEQ ID NO: 7-10.

2. The adjuvant composition of claim 1, wherein the one or more antisense nucleotide sequences comprise uniform modifications of each nucleotide with 2'-O-methyl, 2'-O-ethyl, or 2'-methoxyethyl substituents; uniform replacement of the ribose sugar with a morpholino and phosphorous-containing intersubunit linkages (PMO); dimethylamine-linked phosphate, or methylphosphonates.

3. The adjuvant composition of claim 1, further comprising one or more aminoglycosides.

4. The adjuvant composition of claim 3, wherein the aminoglycoside comprises one or more of Kanamycin A, Amikacin, Tobramycin, Dibekacin, Gentamicin, Sisomicin, Netilmicin, Neomycin B, Neomycin C, Neomycin E (paromomycin), Streptomycin, Plazomicin, or Neo-Fradin.

5. A method for suppressing an IL-10 immune response associated with a vaccine, the method comprising administering a therapeutically effective amount of the adjuvant composition of claim 1 to a subject in need thereof.

6. The method of claim 5, wherein the vaccine is for an infectious disease selected from one or more of Herpes simplex, type 1; Herpes simplex, type 2; encephalitis virus, papillomavirus, Varicella-zoster virus; Epstein-Barr virus; Human cytomegalovirus; Human herpesvirus, type 8; Human papillomavirus; BK virus; JC virus; Smallpox; polio virus, Hepatitis B virus; Human bocavirus; Parvovirus B19; Human astrovirus; Norwalk virus; coxsackievirus; hepatitis A virus; poliovirus; rhinovirus; Hepatitis C virus; yellow fever virus; dengue virus; West Nile virus; Rubella virus; Hepatitis E virus; Human immunodeficiency virus (HIV); Influenza virus, type A or B; Guanarito virus; Junin virus; Lassa virus; Machupo virus; Sabiávirus; Crimean-Congo hemorrhagic fever virus; Ebola virus; Marburg virus; Measles virus; Mumps virus; Parainfluenza virus; Respiratory syncytial virus; Human metapneumovirus; Hendra virus; Nipah virus; Rabies virus; Hepatitis D; Rotavirus; Orbivirus; Coltivirus; Hantavirus; Coronavirus, including SARS-CoV-2, Severe acute respiratory syndrome virus, and Middle East Respiratory Coronavirus; Chikungunya virus; Banna virus, Tuberculosis, or Leishmaniasis.

7. The method of claim 5, wherein the vaccine is for SARS-COV-2, Severe acute respiratory syndrome virus, Middle East Respiratory Coronavirus, Dengue, Influenza, Ebola, Tuberculosis, or Leishmaniasis.

8. The method of claim 5, wherein the adjuvant composition is administered prior to, concurrently with, or following administration of a vaccine.

9. The method of claim 5, wherein the adjuvant composition is administered orally, by injection, or by inhalation/insufflation.

10. The method of claim 5, wherein the adjuvant composition is administered with one or more second adjuvants.

11. The method of claim 10, wherein the second adjuvant comprises one or more of: cationic liposome-DNA complex JVRS-100, aluminum hydroxide vaccine adjuvant, aluminum phosphate vaccine adjuvant, aluminum potassium sulfate adjuvant, alhydrogel, ISCOM(s)™, Freund's Complete Adjuvant, Freund's Incomplete Adjuvant, CpG DNA Vaccine Adjuvant, Cholera toxin, Cholera toxin B subunit, Liposomes, Saponin Vaccine Adjuvant, DDA Adjuvant, Squalene-based Adjuvants, Etx B subunit Adjuvant, IL-12 Vaccine Adjuvant, LTK63 Vaccine Mutant Adjuvant, Titer-Max Gold Adjuvant, Ribi Vaccine Adjuvant, Montanide ISA 720 Adjuvant, Corynebacterium-derived P40 Vaccine Adjuvant, MPL™ Adjuvant, AS04, AS02, Lipopolysaccharide Vaccine Adjuvant, Muramyl Dipeptide Adjuvant, CRL1005, Killed Corynebacterium parvum Vaccine Adjuvant, Montanide ISA 51, Bordetella pertussis component Vaccine Adjuvant, Cationic Liposomal Vaccine Adjuvant, Adamantylamide Dipeptide Vaccine Adjuvant, Arlacel A, VSA-3 Adjuvant, Aluminum vaccine adjuvant, Algal Glucan, Bay R1005, Stearyl Tyrosine, Specol, Algammulin, Calcium Phosphate Gel, CTA1-DD gene fusion protein, DOC/Alum Complex, Gamma Inulin, Gerbu Adjuvant, GM-CSF, GMDP, Recombinant hIFN-γ, interferon-γ, Interleukin-1β, Interleukin-2, Interleukin-7, Sclavo peptide, Rehydragel LV, Rehydragel HPA, Loxoribine, MF59, MTP-PE Liposomes, Murametide, Murapalmitine, D-Murapalmitine, NAGO, Non-Ionic Surfactant Vesicles, PMMA, Protein Cochleates, QS-21, SPT (Antigen Formulation), nanoemulsion vaccine adjuvant, AS03, Quil-A vaccine adjuvant, RC529 vaccine adjuvant, LTR192G Vaccine Adjuvant, E. coli heat-labile toxin, LT, amorphous aluminum hydroxyphosphate sulfate adjuvant, Calcium phosphate vaccine adjuvant, Montanide Incomplete Seppic Adjuvant, Imiquimod, Resiquimod, AF03, Flagellin, Poly(I:C), Abisco-100 vaccine adjuvant, Albumin-heparin microparticles vaccine adjuvant, AS-2 vaccine adjuvant, B7-2 vaccine adjuvant, DHEA vaccine adjuvant, Immunoliposomes Containing Antibodies to Costimulatory Molecules, SAF-1, Sendai Proteoliposomes, Sendai-containing Lipid Matrices, Threonyl muramyl dipeptide (TMDP), Ty Particles vaccine adjuvant, Bupivacaine vaccine adjuvant, D,L-PGL (Polyester poly (D,L-lactide-co-glycolide)) vaccine adjuvant, IL-15 vaccine adjuvant, TK72 vaccine adjuvant, MPL-SE vaccine adjuvant, non-toxic mutant E112K of Cholera Toxin mCT-E112K, and/or Matrix-S.

12. The method of claim 5, wherein the adjuvant is administered with one or more aminoglycosides.

13. The method of claim 12, wherein the aminoglycoside comprises one or more of Kanamycin A, Amikacin, Tobramycin, Dibekacin, Gentamicin, Sisomicin, Netilmicin, Neomycin B, Neomycin C, Neomycin E (paromomycin), Streptomycin, Plazomicin, or Neo-Fradin.

14. A method for suppressing an IL-10 immune response as a treatment of a viral, bacterial, or other pathogen infection, comprising administering a therapeutically effective amount of the antisense adjuvant composition of claim 1 to a subject in need thereof.

15. The method of claim 14, wherein the viral, bacterial, or other pathogen infection is selected from one or more of Herpes simplex, type 1; Herpes simplex, type 2; encephalitis virus, papillomavirus, Varicella-zoster virus; Epstein-Barr virus; Human cytomegalovirus; Human herpesvirus, type 8; Human papillomavirus; BK virus; JC virus; Smallpox; polio virus, Hepatitis B virus; Human bocavirus; Parvovirus B19; Human astrovirus; Norwalk virus; coxsackievirus; hepatitis A virus; poliovirus; rhinovirus; Hepatitis C virus; yellow fever virus; dengue virus; West Nile virus; Rubella virus; Hepatitis E virus; Human immunodeficiency virus (HIV); Influenza virus, type A or B; Guanarito virus; Junin virus; Lassa virus; Machupo virus; Sabiávirus; Crimean-Congo hemorrhagic fever virus; Ebola virus; Marburg virus; Measles virus; Mumps virus; Parainfluenza virus; Respiratory syncytial virus; Human metapneumovirus; Hendra virus; Nipah virus; Rabies virus; Hepatitis D; Rotavirus; Orbivirus; Coltivirus; Hantavirus; Coronavirus, including SARS-COV-2, Severe acute respiratory syndrome virus, and Middle East Respiratory Coronavirus; Chikungunya virus, Banna virus, Tuberculosis, or Leishmaniasis.

16. The method of claim 14, wherein the viral, bacterial, or other pathogen infection is selected from SARS-COV-2, Severe Acute Respiratory Syndrome virus, Middle East Respiratory Coronavirus, Dengue, Influenza, Ebola, Tuberculosis, or Leishmaniasis.

17. The method of claim 14, wherein the adjuvant composition is administered with one or more therapeutics.

18. The method of claim 14, wherein the adjuvant composition is administered prior to, concurrently with, or following administration of a therapeutic.

19. The method of claim 14, wherein the adjuvant composition is administered orally, by injection, or by inhalation/insufflation.

20. The method of claim 14, wherein the antisense inhibitor is administered with one or more aminoglycosides.

21. The method of claim 20, wherein the aminoglycoside comprises one or more of Kanamycin A, Amikacin, Tobramycin, Dibekacin, Gentamicin, Sisomicin, Netilmicin, Neomycin B, Neomycin C, Neomycin E (paromomycin), Streptomycin, Plazomicin, or Neo-Fradin.

22. The adjuvant composition of claim 1, wherein:

the nucleotide sequences complementary to a human interleukin 10 mRNA having a single mismatch is SEQ ID NO: 3; and the nucleotide sequences complementary to a human interleukin 10 receptor alpha mRNA comprising nucleotides having a single mismatch is SEQ ID NO: 8.

\*    \*    \*    \*    \*

SEQUENCE LISTING

```
Sequence total quantity: 17
SEQ ID NO: 1            moltype = DNA  length = 21
FEATURE                 Location/Qualifiers
source                  1..21
                        mol_type = other DNA
                        organism = synthetic construct
SEQUENCE: 1
ggagaaatcg atgctgtgga a                                    21

SEQ ID NO: 2            moltype = DNA  length = 21
```

-continued

```
FEATURE              Location/Qualifiers
source               1..21
                     mol_type = other DNA
                     organism = synthetic construct
SEQUENCE: 2
gtgctggctg tgcatgcctt c                                              21

SEQ ID NO: 3         moltype = DNA   length = 21
FEATURE              Location/Qualifiers
source               1..21
                     mol_type = other DNA
                     organism = synthetic construct
SEQUENCE: 3
gatccttctt tgctgcagga a                                              21

SEQ ID NO: 4         moltype = DNA   length = 20
FEATURE              Location/Qualifiers
source               1..20
                     mol_type = other DNA
                     organism = synthetic construct
SEQUENCE: 4
cccggtaacc ctaagggcag                                                20

SEQ ID NO: 5         moltype = DNA   length = 22
FEATURE              Location/Qualifiers
source               1..22
                     mol_type = other DNA
                     organism = synthetic construct
SEQUENCE: 5
ggagaaatcg atgctgtgga ag                                             22

SEQ ID NO: 6         moltype = DNA   length = 23
FEATURE              Location/Qualifiers
source               1..23
                     mol_type = other DNA
                     organism = synthetic construct
SEQUENCE: 6
cctttccttg gagctgtgca gag                                            23

SEQ ID NO: 7         moltype = DNA   length = 22
FEATURE              Location/Qualifiers
source               1..22
                     mol_type = other DNA
                     organism = synthetic construct
SEQUENCE: 7
cgggcacggc agcatcctgg gc                                             22

SEQ ID NO: 8         moltype = DNA   length = 22
FEATURE              Location/Qualifiers
source               1..22
                     mol_type = other DNA
                     organism = synthetic construct
SEQUENCE: 8
gggctgggca gctcttccct gg                                             22

SEQ ID NO: 9         moltype = DNA   length = 23
FEATURE              Location/Qualifiers
source               1..23
                     mol_type = other DNA
                     organism = synthetic construct
SEQUENCE: 9
ctctattcca tacctgagag ata                                            23

SEQ ID NO: 10        moltype = DNA   length = 21
FEATURE              Location/Qualifiers
source               1..21
                     mol_type = other DNA
                     organism = synthetic construct
SEQUENCE: 10
ggagaaatcg atgctgtgga a                                              21

SEQ ID NO: 11        moltype = DNA   length = 23
FEATURE              Location/Qualifiers
source               1..23
                     mol_type = other DNA
                     organism = synthetic construct
SEQUENCE: 11
ggaagaaatc gatgctgtgg aag                                            23
```

```
SEQ ID NO: 12            moltype = AA   length = 7
FEATURE                  Location/Qualifiers
source                   1..7
                         mol_type = protein
                         organism = synthetic construct
SEQUENCE: 12
RRRRRRG                                                                  7

SEQ ID NO: 13            moltype = RNA   length = 21
FEATURE                  Location/Qualifiers
source                   1..21
                         mol_type = other RNA
                         organism = synthetic construct
SEQUENCE: 13
gaaggcatgc acagccagca c                                                  21

SEQ ID NO: 14            moltype = DNA   length = 21
FEATURE                  Location/Qualifiers
source                   1..21
                         mol_type = other DNA
                         organism = synthetic construct
SEQUENCE: 14
ctgctggctg tgcatgcctt c                                                  21

SEQ ID NO: 15            moltype = DNA   length = 1140
FEATURE                  Location/Qualifiers
source                   1..1140
                         mol_type = other DNA
                         organism = Homo sapiens
SEQUENCE: 15
acacatcagg ggcttgctct tgcaaaacca aaccacaaga cagacttgca aaagaaggca    60
tgcacagctc agcactgctc tgttgcctgg tcctcctgac tggggtgagg gccagcccag   120
gccagggcac ccagtctgag aacagctgca cccacttccc aggcaacctg cctaacatgc   180
ttcgagatct ccgagatgcc ttcagcagag tgaagacttt ctttgtgagt atgattcctt   240
accgcatttc agttatttcc ccaaacctca agttcattct ccttttgttc ttcctgcagc   300
aaatgaagga tcagctggac aacttgttgt taaaggagtc cttgctggag gactttaagg   360
tgagagcagg ggcgggggtgc tggggagtg tgcagcatga ttaagggaag ggagactctg   420
cttcctgatt gcagggaatt gggtttgttt ccttcgcttt gaaaaggaga agtgggaaga   480
tgttaactca gcacatccag cagccagagg gtttacaaag ggctcagtcc cttcgggggag   540
gcttctggtg aaggaggatc gctagaacca agctgtcctc ttaagctagt tgcagcagcc   600
cctcctccca gccacctccg ccaatctctc actcaccttt ggctcctgcc cttagggtta   660
cctgggttgc caagccttgt ctgagatgat ccagttttac ctggaggagg tgatgcccca   720
agctgagaac caagacccag acatcaaggc gcatgtgaac tccctggggg agaacctgaa   780
gaccctcagg ctgaggctac ggcgctgtgt aagtagcaga tcagttttt cccttgcagc   840
ctttctcttt tcttccacag catcgatttc ttccctgtga aaacaagagc aaggccgtgg   900
agcaggtgaa gaatgccttt aataaggtga gcttggatgg tggcagagag ggtctgcaga   960
tccccagaaa ggattttaac tgtatgtttc ttatctctct gcacagctcc aagagaaagg  1020
catctacaaa gccatgagtg agtttgacat cttcatcaac tacatagaag cctacatgac  1080
aatgaagata cgaaactgag acatcagggt ggcgactcta tagactctag gacataaatt  1140

SEQ ID NO: 16            moltype = DNA   length = 1200
FEATURE                  Location/Qualifiers
source                   1..1200
                         mol_type = other DNA
                         organism = Homo sapiens
SEQUENCE: 16
gatgcggcgc gcccaggatg ctgccgtgcc tcgtagtgct gctggcggcg ctcctcagcc    60
tccgtcttgg ctcagacgct catggtaagg ctccgggacg cggcccttcc ctgccctgcc   120
cttctcccca gggacagagc tgcccagccc tccgtctgtg tggtttgaag cagaatttt    180
ccaccacatc ctccactgga cacccatccc aaatcagtct gaaagtacct gctatgaagt   240
ggcgctcctg aggtgaggaa aagggaagag ggaggggggag ggaggagtga atccccgcct   300
gtaggattga gcacaagctc gtttccagtg cctaacctgg tatctcctca ggtatggaat   360
agagtcctgg aactccatct ccaactgtag ccagaccctg tcctatgacc ttaccgcagt   420
gaccttggac ctgtaccaca gcaatggcta ccgggccaga gtgcgggctg tggacggcaa   480
ccggcactcc aactgaccg tcaccaacac ccgcttctct gtggatgaag gtgcttttcc   540
tcccttgact tagaacatgg ctctgaagtc ccttccagcc aggaactcta gtctagagct   600
tttctgtcta ttaccatagc tcaccatgtc tgccagcctc cctggccgga gaactagttg   660
ccatttgttg aagagactgt tctttttccca ttgtgtgttc ttggcccctt tgttgaaaat   720
caattgtggg tttatttctg ggctgtccat catattccat tggttgatgc atctgatttt   780
agggtatatg tatttttaat gtgctcccca agaagtcctt acattctgct gcattgacaa   840
acctgtggcc aagtttttagg cctaggttct aattaagctt aattctggag gcaaagtctc   900
ggcgggggaca cccaggccct cctcagccct caagtctcat ggtattcccc cccacccaa   960
ctccatttag tgactctgac agttggcagt gtgaacctga agatccacaa tggcttcatc  1020
ctcgggaaga ttcagctacc caggcccaag atggcccccg caaatgacac atatgaaagc  1080
atcttcagtc acttccgaga gtatgagatt gccattcgca aggtgccggg aaacttcacg  1140
gtatgggggtt ccccaaggcc ccagggccag aactcccttg cttccctgt cccctgggct  1200

SEQ ID NO: 17            moltype = AA   length = 14
FEATURE                  Location/Qualifiers
```

-continued

```
MOD_RES              13
                     note = X13 is 6-aminohexanoic acid
MOD_RES              5
                     note = X5 is 6-aminohexanoic acid
MOD_RES              2
                     note = X2 is 6-aminohexanoic acid
MOD_RES              11
                     note = X11 is 6-aminohexanoic acid
MOD_RES              14
                     note = A14 is beta-alanine
source               1..14
                     mol_type = protein
                     organism = synthetic construct
SEQUENCE: 17
RXRRXRRXRR XRXA                                             14
```